United States Patent
Sendai

(10) Patent No.: US 7,102,142 B2
(45) Date of Patent: Sep. 5, 2006

(54) METHOD OF APPARATUS FOR GENERATING FLUORESCENCE DIAGNOSTIC INFORMATION

(75) Inventor: Tomonari Sendai, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 239 days.

(21) Appl. No.: 10/445,061

(22) Filed: May 27, 2003

(65) Prior Publication Data

US 2003/0218137 A1 Nov. 27, 2003

(30) Foreign Application Priority Data

May 27, 2002 (JP) ............... 2002-152605

(51) Int. Cl.
G01N 21/64 (2006.01)
(52) U.S. Cl. .................................. 250/461.1
(58) Field of Classification Search ............. 250/461, 250/459, 461.1
See application file for complete search history.

(56) References Cited

U.S. PATENT DOCUMENTS 4,718,417 A * 1/1988 Kittrell et al. ............. 606/7
5,421,337 A * 6/1995 Richards-Kortum et al. ..... 600/477
6,577,391 B1 * 6/2003 Faupel et al. ............. 356/337

FOREIGN PATENT DOCUMENTS

JP 6-54792 A 3/1994
JP 10-225436 A 8/1998

* cited by examiner

Primary Examiner—David Porta
Assistant Examiner—Djura Malevic
(74) Attorney, Agent, or Firm—Sughrue Mion, PLLC

(57) ABSTRACT

First fluorescence diagnostic information reflecting a first characteristic value obtained on the basis of first fluorescence information on fluorescence emitted from an object part exposed to first stimulating light is output. Second fluorescence diagnostic information reflecting a second characteristic value obtained on the basis of second fluorescence information on fluorescence emitted from an object part exposed to second stimulating light is output. The wavelength of the first stimulating light is such that when the first stimulating light is projected onto clean object parts different in properties, different first characteristic values are obtained from the different object parts, and the wavelength of the second stimulating light is such that when the second stimulating light is projected onto a clean object part and an unclean object part, different second characteristic values are obtained from the clean object part and the unclean object part.

23 Claims, 12 Drawing Sheets

FIG.13

[Graph showing relative intensity vs wavelength (nm) from 400 to 750 nm, comparing NORMAL TISSUE (dashed curve peaking near 480 nm) and DISEASED TISSUE (solid curve with smaller peak near 660 nm)]

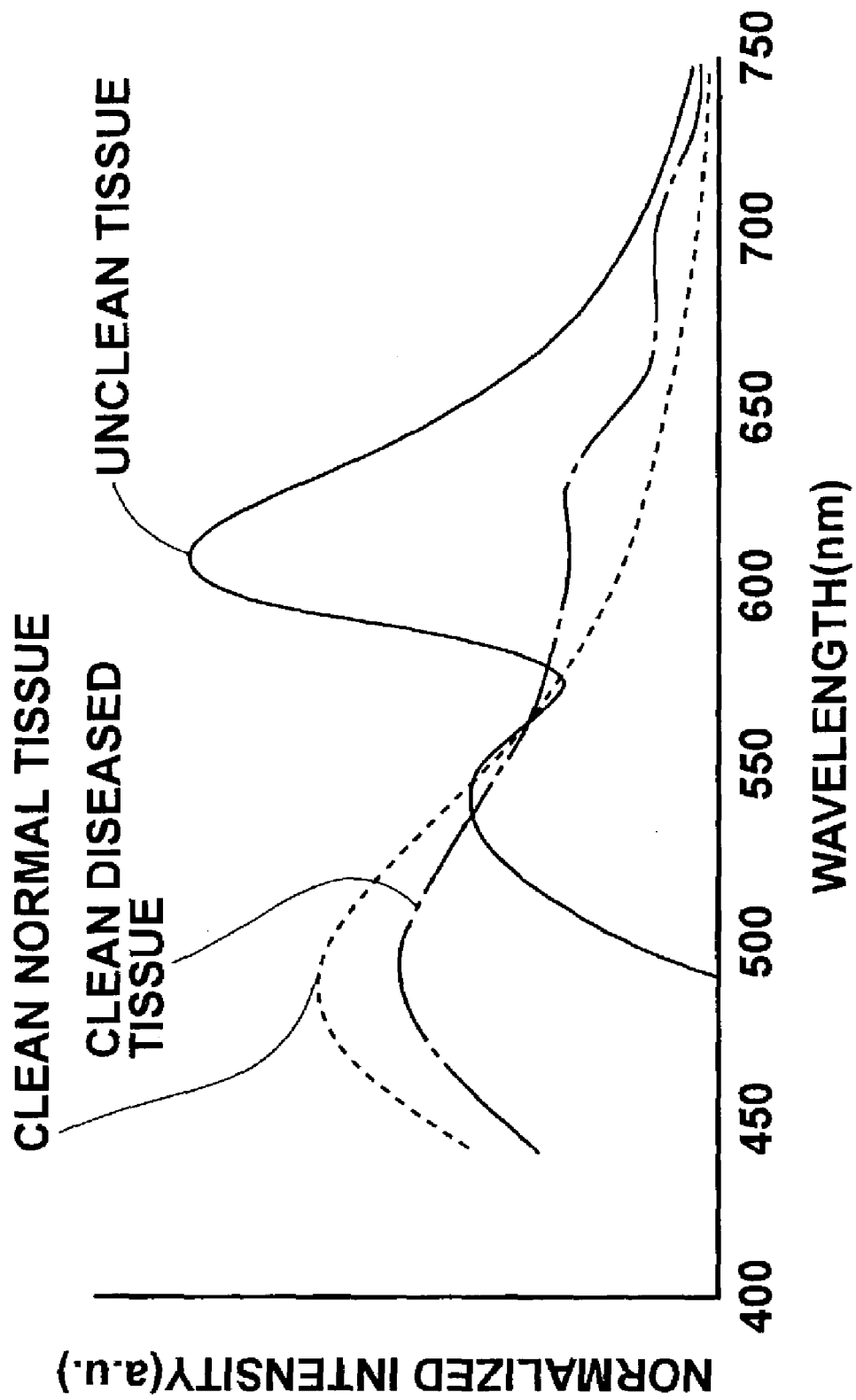

_US 7,102,142 B2_

METHOD OF APPARATUS FOR GENERATING FLUORESCENCE DIAGNOSTIC INFORMATION

BACKGROUND OF THE INVENTION

1. Field of the Invention

This invention relates to a method of and apparatus for generating fluorescence diagnostic information reflecting properties of tissue of an object part on the basis of fluorescence emitted from the object part.

2. Description of the Related Art

There has been proposed a fluorescence diagnostic information generating apparatus which projects stimulating light of a predetermined wavelength onto an object part such as an organic body and outputs fluorescence diagnostic information such as a fluorescence diagnostic image representing properties of tissue of the object part on the basis of fluorescence emitted from the object part. Such fluorescence diagnostic information generating apparatuses can be divided into those which output fluorescence diagnostic information on the basis of fluorescence emitted from the object part which has been caused to absorb a fluorescence agent and those which output fluorescence diagnostic information on the basis of autofluorescence emitted from the object part itself without use of a fluorescence agent. In this specification, the fluorescence emitted from the object part which has been caused to absorb a fluorescence agent will be sometimes referred to as "the agent fluorescence" and the fluorescence diagnostic information generating apparatus of the former type will be sometimes referred to as "the agent fluorescence diagnostic information generating apparatus", hereinbelow. Whereas, the fluorescence diagnostic information generating apparatus of the latter type will be sometimes referred to as "the autofluorescence diagnostic information generating apparatus", hereinbelow. The fluorescence diagnostic information generating apparatus is generally incorporated in an endoscope which is inserted into a body cavity, a colposcope, a surgical microscope or the like.

For example, the fluorescence diagnostic information generating apparatus includes an apparatus which outputs a fluorescence diagnostic image on the basis of the intensity of fluorescence emitted from an organic tissue which has been exposed to stimulating light. As shown in FIG. 13, the intensity of fluorescence emitted from a diseased tissue is lower than that of fluorescence emitted from a normal tissue. Accordingly, normal tissues can be distinguished from diseased tissues on the basis of fluorescence diagnostic image based on the intensity of fluorescence.

In the case where the fluorescence diagnostic information generating apparatus is incorporated in an endoscope, the distance between the stimulating light source and the object part cannot be uniform due to the protruding portions and the recessed portions of the object part and the illuminance of the stimulating light at the surface of the object part cannot be uniform. Generally intensity of fluorescence emitted from a normal tissue is proportional to the illuminance of the stimulating light, and the illuminance of the stimulating light reduces in inverse proportion to the square of the distance. Accordingly, fluorescence emitted from a diseased tissue at a smaller distance from the stimulating light source can be higher in intensity than that emitted from a normal tissue at a larger distance from the stimulating light source, and judgment on the properties of the object tissue solely on the basis of the intensity of fluorescence can result in an erroneous judgment.

In order to avoid such an erroneous judgment, there has been proposed a fluorescence diagnostic information generating apparatus which outputs the fluorescence diagnostic information on the basis of the yield of fluorescence which is a value based on the ratio of the intensity of the stimulating light which the object part receives to the intensity of fluorescence emitted from the object part and does not depend upon the distance or the angle at which the stimulating light is projected onto the object part.

However, since the stimulating light in an ultraviolet region to a visible region is absorbed in different amounts by different substances of the object part, the intensity distribution of the stimulating light projected onto the object part cannot be accurately measured by measuring the intensity distribution of the reflected stimulating light, and accordingly, it has been difficult to obtain the yield of fluorescence on the basis of the intensity distribution of the reflected stimulating light.

As a method of obtaining the yield of fluorescence (or a value reflecting the yield of fluorescence), there has been proposed a method in which near-infrared light which undergoes more uniform absorption as compared with the stimulating light in an ultraviolet region to a visible region is projected onto the object part as reference light, and the value obtained by dividing the intensity of fluorescence by the intensity of the reflected near-infrared light is employed as a value reflecting the yield of fluorescence. That is, by obtaining the value reflecting the yield of fluorescence, terms representing the intensity of fluorescence depending upon the distance between the stimulating light source and the object part and/or the distance between the fluorescence receiving portion and the object part are cancelled.

Further, the shape of spectrum of fluorescence emitted from a normal tissue differs from that of fluorescence emitted from a diseased tissue as shown in FIG. 13. A fluorescence diagnostic information generating apparatus based on the difference has been developed. For example, as disclosed in Japanese Unexamined Patent Publication No. 6(1994)-54792, there is proposed an apparatus which outputs fluorescence diagnostic information on the basis of a G/R ratio, the ratio of the intensity of fluorescence in a green wavelength band to the intensity of fluorescence in a red wavelength band.

Further, we, this applicant, have proposed, in Japanese Unexamined Patent Publication No. 10(1998)-225436, an apparatus which outputs fluorescence diagnostic information reflecting a normalized intensity of fluorescence, an intensity of narrow wavelength band light from the object part normalized by an intensity of broad wavelength band light from the object part. In the apparatus, image data in a narrow wavelength band near 480 nm and image data in a broad wavelength band from near 430 nm to near 730 nm are obtained and a normalized intensity of fluorescence is obtained by dividing the values of pixels in the image data in the narrow wavelength band by the values of pixels in the image data in the broad wavelength band. Then a pseudo-color image based on the normalized intensity of fluorescence, for instance, a color image in which color changes from green to red as the normalized intensity of fluorescence is reduced, is output as a fluorescence diagnostic image. That is, by obtaining the normalized intensity of fluorescence, terms representing the intensity of fluorescence depending upon the distance between the stimulating light source and the object part and/or the distance between the fluorescence receiving portion and the object part are cancelled, a fluorescence diagnostic image based on solely values reflecting the difference in fluorescence spectrum can be output.

The object tissue is sometimes stained with disturbance factors such as blood, mucus, digestive fluid, saliva, foam, residue and the like. When an organic tissue stained with such a disturbance factor (will be referred to as "unclean tissue", hereinbelow) is exposed to the stimulating light, the disturbance factor also emits fluorescence. Fluorescence emitted from an unclean tissue is sometimes confusing with fluorescence emitted from a diseased tissue in the normalized intensity of fluorescence and/or the yield of fluorescence.

Generation of fluorescence diagnostic image on the basis of the normalized intensity of fluorescence will be described, hereinbelow, by way of example. FIG. 14 is a view showing the shapes of spectra of fluorescences emitted from a clean normal tissue (the dotted line), a clean diseased tissue (the chained line) and an unclean tissue (the solid line) upon exposure to stimulating light of 410 nm, wherein the intensity of fluorescence is normalized so that the integrated value becomes 1.

In the case where image data in a narrow wavelength band near 480 nm and image data in a broad wavelength band from near 430 nm to near 730 nm are obtained, a normalized intensity of fluorescence is obtained by dividing the values of pixels in the image data in the narrow wavelength band by the values of pixels in the image data in the broad wavelength band, and a pseudo-color image based on the normalized intensity of fluorescence, for instance, a color image in which color changes from green to red as the normalized intensity of fluorescence is reduced, is output as a fluorescence diagnostic image, pseudo-color is generally allocated so that the normalized intensity of fluorescence emitted from the normal tissue is displayed in green and the normalized intensity of fluorescence emitted from the diseased tissue is displayed in red. Generally, normalized intensities of fluorescence not higher than the normalized intensity of fluorescence emitted from the diseased tissue are all displayed in red. Since the normalized intensity of fluorescence emitted from the unclean tissue is generally close to or lower than the normalized intensity of fluorescence emitted from the diseased tissue, the normalized intensity of fluorescence emitted from the unclean tissue is also displayed in red. That is, both the normalized intensity of fluorescence emitted from the diseased tissue and the normalized intensity of fluorescence emitted from the unclean tissue are displayed in red. When the viewer distinguishes normal tissues from diseased tissues on the basis of a fluorescence diagnostic image thus obtained, the viewer can mistake an unclean tissue for a diseased tissue, whereby the tissue-property distinguishing accuracy is deteriorated.

Since many of unclean tissues emit weak fluorescence as a clean diseased tissue, even if the fluorescence diagnostic image is generated on the basis of the intensity of fluorescence or the yield of fluorescence, the viewer can mistake an unclean tissue for a diseased tissue, whereby the tissue-property distinguishing accuracy is deteriorated.

SUMMARY OF THE INVENTION

In view of the foregoing observations and description, the primary object of the present invention is to provide a method of and apparatus for generating fluorescence diagnostic information which can suppress mistaking an unclean tissue for a clean diseased tissue, thereby improving the tissue-property distinguishing accuracy.

In accordance with a first aspect of the present invention, there is provided a method of generating fluorescence diagnostic information comprising the steps of detecting first fluorescence information on fluorescence emitted from an object part exposed to first stimulating light, obtaining a first characteristic value on the basis of the first fluorescence information, and outputting a first fluorescence diagnostic information reflecting the first characteristic value, and detecting second fluorescence information on fluorescence emitted from the object part exposed to second stimulating light, obtaining a second characteristic value on the basis of the second fluorescence information, and outputting a second fluorescence diagnostic information reflecting the second characteristic value, wherein the wavelength of the first stimulating light is such that when the first stimulating light is projected onto clean object parts different in properties, different first characteristic values are obtained on the basis of the respective pieces of fluorescence information on fluorescences emitted from the object parts, and the wavelength of the second stimulating light is such that when the second stimulating light is projected onto a clean object part and an unclean object part, different second characteristic values are obtained on the basis of the respective pieces of fluorescence information on fluorescences emitted from the clean object part and the unclean object part.

In accordance with a second aspect of the present invention, there is provided a method of generating fluorescence diagnostic information comprising the steps of detecting first fluorescence information on fluorescence emitted from an object part exposed to first stimulating light, and obtaining a first characteristic value on the basis of the first fluorescence information, detecting second fluorescence information on fluorescence emitted from the object part exposed to second stimulating light, and obtaining a second characteristic value on the basis of the second fluorescence information, and creating fluorescence diagnostic information reflecting the first and second characteristic values and outputting the fluorescence diagnostic information, wherein the wavelength of the first stimulating light is such that when the first stimulating light is projected onto clean object parts different in properties, different first characteristic values are obtained on the basis of the respective pieces of fluorescence information on fluorescences emitted from the object parts, and the wavelength of the second stimulating light is such that when the second stimulating light is projected onto a clean object part and an unclean object part, different second characteristic values are obtained on the basis of the respective pieces of fluorescence information on fluorescences emitted from the clean object part and the unclean object part.

In accordance with a third aspect of the present invention, there is provided an apparatus for generating fluorescence diagnostic information comprising a first stimulating light projecting means which projects first stimulating light onto an object part, a first detecting means which detects first fluorescence information on fluorescence emitted from the object part exposed to the first stimulating light, a first characteristic value obtaining means which obtains a first characteristic value on the basis of the first fluorescence information, a first fluorescence diagnostic information generating means which outputs a first fluorescence diagnostic information reflecting the first characteristic value, a second stimulating light projecting means which projects second stimulating light onto the object part, a second detecting means which detects second fluorescence information on fluorescence emitted from the object part exposed to the second stimulating light, a second characteristic value obtaining means which obtains a second characteristic value on the basis of the second fluorescence information, and a second fluorescence diagnostic information generating means which outputs a second fluorescence diagnostic information reflecting the second characteristic value, wherein the wavelength of the first stimulating light is such that when the first stimulating light is projected onto clean object parts different in properties, different first characteristic values are obtained on the basis of the respective pieces of fluorescence information on fluorescences emitted from the object parts, and the wavelength of the second stimulating light is such that when the second stimulating light is projected onto a clean object part and an unclean object part, different second characteristic values are obtained on the basis of the respective pieces of fluorescence information on fluorescences emitted from the clean object part and the unclean object part.

In accordance with a fourth aspect of the present invention, there is provided an apparatus for generating fluorescence diagnostic information comprising a first stimulating light projecting means which projects first stimulating light onto an object part, a first detecting means which detects first fluorescence information on fluorescence emitted from the object part exposed to the first stimulating light, a first characteristic value obtaining means which obtains a first characteristic value on the basis of the first fluorescence information, a second stimulating light projecting means which projects second stimulating light onto the object part, a second detecting means which detects second fluorescence information on fluorescence emitted from the object part exposed to the second stimulating light, a second characteristic value obtaining means which obtains a second characteristic value on the basis of the second fluorescence information, and a fluorescence diagnostic information generating means which outputs a fluorescence diagnostic information reflecting the first and second characteristic values, wherein the wavelength of the first stimulating light is such that when the first stimulating light is projected onto clean object parts different in properties, different first characteristic values are obtained on the basis of the respective pieces of fluorescence information on fluorescences emitted from the object parts, and the wavelength of the second stimulating light is such that when the second stimulating light is projected onto a clean object part and an unclean object part, different second characteristic values are obtained on the basis of the respective pieces of fluorescence information on fluorescences emitted from the clean object part and the unclean object part.

In the method and apparatus described above, the expression "characteristic values are different" need not be limited to meaning the case where the characteristic values are entirely different from each other but may include a case where the characteristic values partly overlap each other so long as they can be substantially separated from each other. For example, the case where distributions of characteristic values obtained from a plurality of clean object parts and distributions of those obtained from a plurality of unclean parts can be substantially separated from each other may be included in cases where characteristic values are different.

The fluorescence diagnostic information generating means may comprise a storage means which stores a first reference value created in advance on the basis of a first characteristic value obtained from at least one of a known clean normal tissue and a known clean diseased tissue, and a second reference value created in advance on the basis of a second characteristic value obtained from at least one of a known clean tissue and a known unclean tissue, and a judgment means which judges whether the object part is on the side of the known clean diseased part on the basis of a first characteristic value obtained from the object part and the first reference value, and judges whether the object part is on the side of the known unclean part on the basis of a second characteristic value obtained from the object part and the second reference value, and may output as the fluorescence diagnostic information the result of judgment of the judgment means.

As the characteristic value, for instance, the intensity of fluorescence, the shape of spectrum of fluorescence, a normalized intensity of fluorescence reflecting the shape of spectrum of fluorescence or the yield of fluorescence can be employed. The "normalized intensity of fluorescence" is a value which reflects the shape of spectrum of fluorescence, e.g., a proportion of intensities of fluorescence obtained from the object part in different wavelength bands. For example, the "normalized intensity of fluorescence" may be obtained by dividing an intensity of fluorescence in a narrow wavelength band (e.g., 430 nm to 530 nm) by an intensity of fluorescence in a broad wavelength band (e.g., the entire wavelength band or an wavelength band from 430 nm to 730 nm). The "normalized intensity of fluorescence" may be obtained on the basis of a proportion of intensities of fluorescence obtained from the object part in a pair of narrow wavelength bands (e.g., a narrow wavelength band near 480 nm and a narrow wavelength band near 630 nm).

The "yield of fluorescence" means a ratio of the intensity of the stimulating light which the object part receives to the intensity of fluorescence emitted from the object part. The "yield of fluorescence" as used here need not be strictly a ratio of the intensity of the stimulating light which the object part receives to the intensity of fluorescence emitted from the object part so long as it reflects the "yield of fluorescence". For example, the "yield of fluorescence" may be obtained as a ratio of the intensity of a reference light (as substitution of the intensity of the stimulating light which the object part receives) and the intensity of fluorescence emitted from the object part. The reference light maybe near-infrared light which is relatively uniform in reflecting properties independent of the kind of the tissue. Normal illumination light may be employed as the reference light though the accuracy slightly deteriorates. In the case of, for instance, an endoscope, the intensity of fluorescence may be employed as the yield of fluorescence if fluctuation in the distance between the end face of the endoscope and the object part can be held small.

When the wavelength of the first stimulating light is near 410 nm, the wavelength of the second stimulating light may be substantially in the range of 350 nm to 390 nm or in the range of 470 nm to 520 nm. It is preferred that the wavelength of the first stimulating light be in the range of 400 nm to 420 nm.

When the wavelength of the second stimulating light is in the range of 350 nm to 390 nm and the second characteristic value is the normalized intensity of fluorescence, one of the different wavelength bands may be a wavelength band near 460 nm. When the wavelength of the second stimulating light is in the range of 470 nm to 520 nm and the second characteristic value is the normalized intensity of fluorescence, one of the different wavelength bands may be a wavelength band near 550 nm.

The system for generating fluorescence diagnostic information of the present invention may be formed as an endoscope which is partly or wholly inserted inside an organic body.

The first stimulating light projecting means may be provided with a Ga—N semiconductor laser as a source of the first stimulating light. The second stimulating light projecting means may be provided with a Ga—N semiconductor laser as a source of the second stimulating light.

We have investigated characteristic values of fluorescences emitted from a clean organic tissue and an unclean organic tissue for various wavelengths of stimulating light and found that the characteristic value obtained from fluorescence information on fluorescence emitted from a clean organic tissue sometimes differ from the characteristic value obtained from fluorescence information on fluorescence emitted from an unclean organic tissue.

For example, FIG. 1 shows the shapes of spectra of fluorescences emitted from a clean normal tissue (the dotted line), a clean diseased tissue (the chained line) and an unclean tissue (the solid line) upon exposure to stimulating light of 360 nm. As can be understood from FIG. 1, the fluorescence emitted from an unclean tissue differs from the fluorescences emitted from a clean normal tissue and a clean diseased tissue in shape of spectrum. Accordingly, the normalized intensities of fluorescence obtained from fluorescences emitted from a clean normal tissue and a clean diseased tissue differ from that obtained from fluorescence emitted from an unclean organic tissue, which means that whether an object part is clean or unclean can be distinguished on the basis of the normalized intensity of fluorescence emitted from the object part upon exposure to stimulating light of 360 nm.

Whereas FIG. 2 shows the shapes of spectra of fluorescences emitted from a clean normal tissue (the dotted line), a clean diseased tissue (the chained line) and an unclean tissue (the solid line) upon exposure to stimulating light of 500 nm. As can be understood from FIG. 2, the fluorescence emitted from an unclean tissue differs from the fluorescences emitted from a clean normal tissue and a clean diseased tissue in shape of spectrum. Accordingly, the normalized intensities of fluorescence obtained from fluorescences emitted from a clean normal tissue and a clean diseased tissue differ from that obtained from fluorescence emitted from an unclean organic tissue, which means that whether an object part is clean or unclean can be distinguished on the basis of the normalized intensity of fluorescence emitted from the object part upon exposure to stimulating light of 500 nm. On the other hand, the properties of tissue of an object part can be distinguished on the basis of fluorescence emitted from the object part upon exposure to stimulating light of 410 nm, as is well known.

That is, in accordance with a method of the first aspect of the present invention and an apparatus of the third aspect of the present invention, a clean diseased tissue and an unclean tissue can be distinguished from a clean normal tissue on the basis of the first fluorescence diagnostic information reflecting the first characteristic value and a clean diseased tissue can be distinguished from an unclean tissue on the basis of the second fluorescence diagnostic information reflecting the second characteristic value. Accordingly, an unclean tissue stained with disturbance factors and a clean diseased tissue can be distinguished from each other on the basis of both the first fluorescence diagnostic information and the second fluorescence diagnostic information, whereby mistaking an unclean tissue for a clean diseased tissue can be suppressed and the tissue-property distinguishing accuracy can be improved.

In accordance with a method of the second aspect of the present invention and an apparatus of the fourth aspect of the present invention, whether the object part is a clean diseased tissue or an unclean tissue can be known on the basis of the fluorescence diagnostic information reflecting the first and second characteristic values, whereby mistaking an unclean tissue for a clean diseased tissue can be suppressed and the tissue-property distinguishing accuracy can be improved.

When the fluorescence diagnostic information generating means comprises a storage means which stores a first reference value created in advance on the basis of a first characteristic value obtained from at least one of a known clean normal tissue and a known clean diseased tissue, and a second reference value created in advance on the basis of a second characteristic value obtained from at least one of a known clean tissue and a known unclean tissue, and a judgment means which judges whether the object part is on the side of the known clean diseased part on the basis of a first characteristic value obtained from the object part and the first reference value and judges whether the object part is on the side of the known unclean part on the basis of a second characteristic value obtained from the object part and the second reference value, and outputs as the fluorescence diagnostic information the result of judgment of the judgment means, the viewer can easily recognize the result of judgment.

When the first characteristic value is a normalized intensity of fluorescence reflecting the shape of spectrum of fluorescence or the yield of fluorescence and the second characteristic value is a normalized intensity of fluorescence reflecting the shape of spectrum of fluorescence or the yield of fluorescence, properties of the object part can be distinguished on the basis of the shape of spectrum of fluorescence or the yield of fluorescence, whereby the tissue-property distinguishing accuracy can be further improved.

In order to improve the tissue-property distinguishing accuracy, it is preferred that the wavelength of the first stimulating light be near 410 nm, and the wavelength of the second stimulating light be in the range of 350 nm to 390 nm or in the range of 470 nm to 520 nm.

When the wavelength of the second stimulating light is in the range of 350 nm to 390 nm and the normalized intensity of fluorescence is employed as the second characteristic value, it is preferred that a wavelength band near 460 nm where, as shown in FIG. 1, there is a remarkable difference between the shape of spectrum of fluorescence emitted from an unclean tissue (the solid line) and that of fluorescence emitted from a clean tissue (the dotted line and the chained line) be employed as one of the different wavelength bands for calculating a proportion of intensities of fluorescence obtained from the object part, which reflects the shape of spectrum of the fluorescence.

When the wavelength of the second stimulating light is in the range of 470 nm to 520 nm and the normalized intensity of fluorescence is employed as the second characteristic value, it is preferred that a wavelength band near 550 nm where, as shown in FIG. 2, there is a remarkable difference between the shape of spectrum of fluorescence emitted from an unclean tissue (the solid line) and that of fluorescence emitted from a clean tissue (the dotted line and the chained line) be employed as one of the different wavelength bands for calculating a proportion of intensities of fluorescence obtained from the object part, which reflects the shape of spectrum of the fluorescence.

BRIEF DESCRIPTION OF THE DRAWINGS

FIG. 13 is a view showing the shapes of spectra of fluorescences emitted from a normal tissue and a diseased tissue, and FIG. 14 is a view showing the shapes of spectra of fluorescences emitted from a clean normal tissue, a clean diseased tissue and an unclean tissue upon exposure to stimulating light of 410 nm.

DESCRIPTION OF THE PREFERRED EMBODIMENTS

Figure 3:
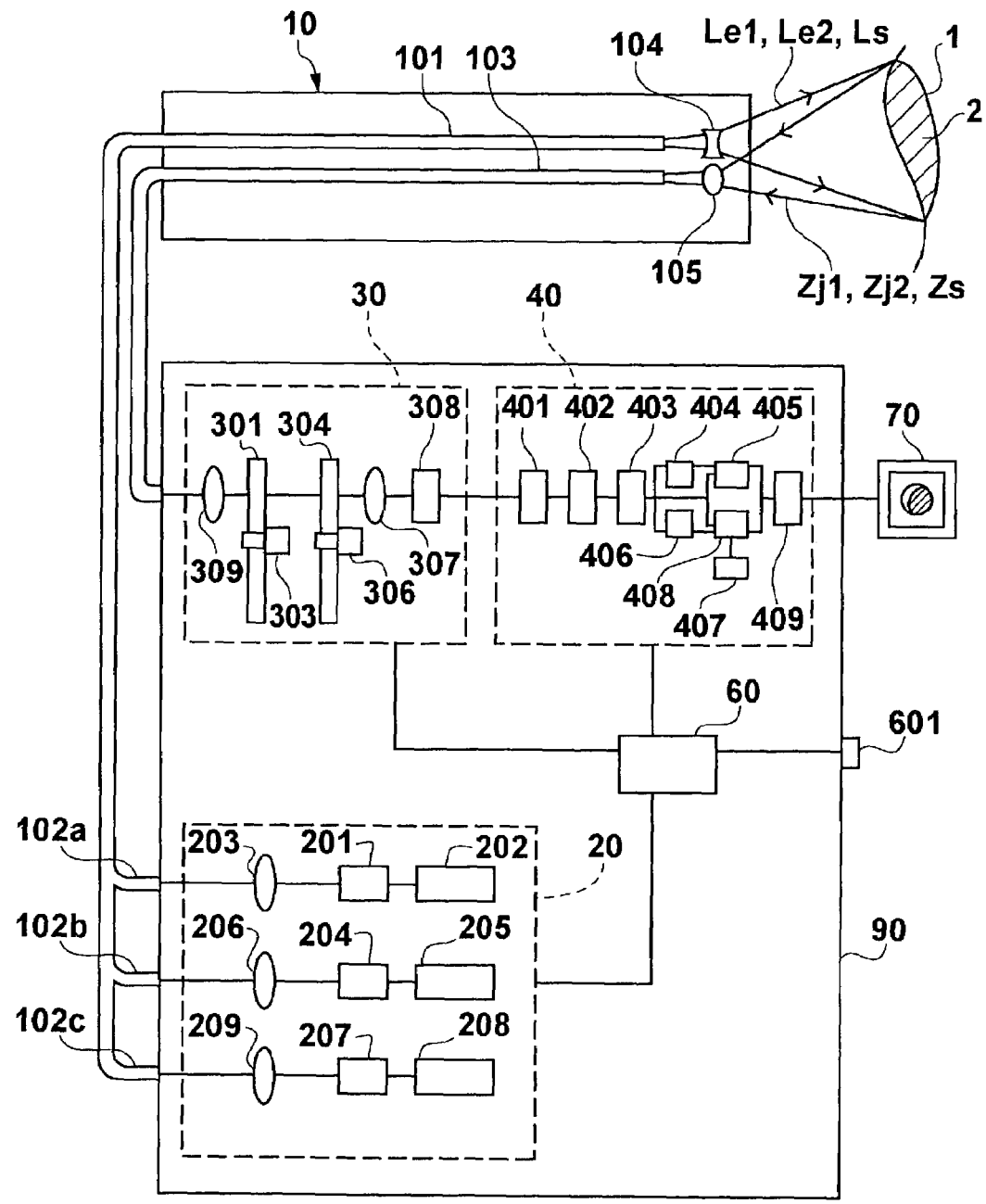
FIG. 3 is a view showing in brief a fluorescence endoscope in accordance with a first embodiment of the present invention.

A fluorescence endoscope in accordance with a first embodiment of the present invention will be described with reference to FIGS. 3 to 5, hereinbelow.

The fluorescence endoscope works either in a fluorescence diagnosis mode or in a disturbance judgment mode which are switched by operation of an input system (a foot switch) 601. In the fluorescence diagnosis mode, stimulating light Le1 of a wavelength of 410 nm is projected onto an object part 1, and a fluorescence diagnostic image is displayed on a monitor 70, the fluorescence diagnostic image being a pseudo-color image obtained by allocating pseudo-colors on the basis of an yield of fluorescence emitted from the object part 1, and in the disturbance judgment mode, stimulating light Le2 of a wavelength of 500 nm is projected onto the object part 1 and a disturbance judgment image is displayed on the monitor 70, the disturbance judgment image being a pseudo-color image obtained by allocating a pseudo-color to each pixel 2 of the object part 1 (an area corresponding to each pixel of the image pick-up tube, e.g., CCD) on the basis of the degree of influence of the disturbance factor thereon calculated according to fluorescence emitted from the object part 1.

In the fluorescence diagnosis mode, fluorescence image data in a broad wavelength band of 430 nm to 700 nm is obtained on the basis of fluorescence emitted from the object part 1 upon exposure to the stimulating light Le1 (This fluorescence image data will be referred to as "the broad-band fluorescence image data (Le1)", hereinbelow), IR reflection image data is obtained on the basis of reflected reference light Ls (near-infrared light) reflected by the object part 1 when the reference light Ls is projected onto the object part 1, a value reflecting the yield of fluorescence (will be referred to simply as "the yield of fluorescence (Le1)", hereinbelow) is obtained pixel by pixel by dividing the value of each pixel of the broad-band fluorescence image data (Le1) by the value of the corresponding pixel of the IR reflection image data, color information for each pixel is generated on the basis of the yield of fluorescence (Le1) for the pixel, brightness information for each pixel is generated on the basis of the value of the corresponding pixel of the IR reflection image data, and a fluorescence diagnostic image is displayed on the monitor 70 on the basis of combination of the color information and the brightness information. In the disturbance judgment mode, fluorescence image data in a narrow wavelength band of 530 nm to 570 nm is obtained on the basis of fluorescence emitted from the object part 1 upon exposure to the stimulating light Le2 (This fluorescence image data will be referred to as "the narrow-band fluorescence image data (Le2)", hereinbelow), fluorescence image data in a broad wavelength band of 530 nm to 800 nm is obtained on the basis of fluorescence emitted from the object part 1 upon exposure to the stimulating light Le2 (This fluorescence image data will be referred to as "the broad-band fluorescence image data (Le2)", hereinbelow), IR reflection image data is obtained on the basis of reflected reference light Ls (near-infrared light) reflected by the object part 1 when the reference light Ls is projected onto the object part 1, a value reflecting the normalized intensity of fluorescence (will be referred to simply as "the normalized intensity of fluorescence (Le2)", hereinbelow) is obtained pixel by pixel by dividing the value of each pixel of the narrow-band fluorescence image data (Le2) by the value of the corresponding pixel of the broad-band fluorescence image data (Le2), color information for each pixel is generated on the basis of the degree of influence of the disturbance factor for the pixel calculated from the normalized intensity of fluorescence (Le2) for the pixel, brightness information for each pixel is generated on the basis of the value of the corresponding pixel of the IR reflection image data, and a disturbance judgment image is displayed on the monitor 70 on the basis of combination of the color information and the brightness information.

The fluorescence endoscope of the first embodiment comprises a scope section 10 which is inserted into a suspected diseased part of a patient, an illumination unit 20 provided with sources of the stimulating light Le1, the stimulating light Le2, and the reference light Ls, an image taking unit (a CCD image pick-up device) 30 which takes fluorescence images Zj1 and Zj2 and an IR reflection image Zs, a fluorescence image processing unit 40, a controller 60 which is connected to the units and controls the timing of operation of the units, and a monitor 70 which displays a visible image on the basis of fluorescence diagnostic image data or disturbance judgment image data output from the fluorescence image processing unit 40. The fluorescence image processing unit 40 generates color information for each pixel on the basis of the yield of fluorescence (Le1) for the pixel and brightness information for each pixel on the basis of the value of the corresponding pixel of the IR reflection image data, and outputs a video signal representing a fluorescence diagnostic image on the basis of combination of the color information and the brightness information in the fluorescence diagnosis mode, and generates color information for each pixel on the basis of the normalized intensity of fluorescence (Le2) for the pixel and brightness information for each pixel on the basis of the value of the corresponding pixel of the IR reflection image data, and outputs a video signal representing a disturbance judgment image on the basis of combination of the color information and the brightness information in the disturbance judgment mode. The controller 60 is connected to the input system 601. The illumination unit 20, the image taking unit 30, the fluorescence image processing unit 40 and the controller 60 form a processor section 90. The scope section 10 and the processor section 90 are connected by way of a connector (not shown) and the processor section 90 and the monitor 70 are connected by way of a connector (not shown).

A light guide 101 and an image fiber 103 extend inside the scope section 10 up to the front end of the endoscope. An illumination lens 104 is provided on the front end of the light guide 101, and a condenser lens 105 is provided on the front end of the image fiber 103. The image fiber 103 is a multi-component glass fiber.

The light guide 101 comprises a light guide 102a for guiding the stimulating light Le1, a light guide 102b for guiding the stimulating light Le2, and a light guide 102c for guiding the reference light Ls which are bundled together and integrated into a cable. The light guides 102a to 102c are connected to the illumination unit 20 and the image fiber 103 is connected to the image taking unit 30 at its one end.

The illumination unit 20 comprises a stimulating light source unit comprising a Ga—N semiconductor laser 201 which emits the stimulating light Le1 of a wavelength of 410 nm and a power source 202 for the semiconductor laser 201, a stimulating light source unit comprising a Ga—N semiconductor laser 204 which emits the stimulating light Le2 of a wavelength of 500 nm and a power source 205 for the semiconductor laser 204, and a reference light source unit comprising a semiconductor laser 207 which emits near-infrared light as the reference light Ls and a power source 208 for the semiconductor laser 207.

The image taking unit 30 comprises a variable stimulating light cut filter means 301 which is a combination of two kinds of optical filters, a filter drive system 303 which rotates the variable stimulating light cut filter means 301, a variable filter means 304 which is a combination of four kinds of optical filters, a filter drive system 306 which rotates the variable filter means 304, and a CCD image taking device 308 which takes by way of an optical lens 307 fluorescence images Zj1 and Zj2 and an IR reflection image Zs passing through the variable filter means 304.

Figure 4:
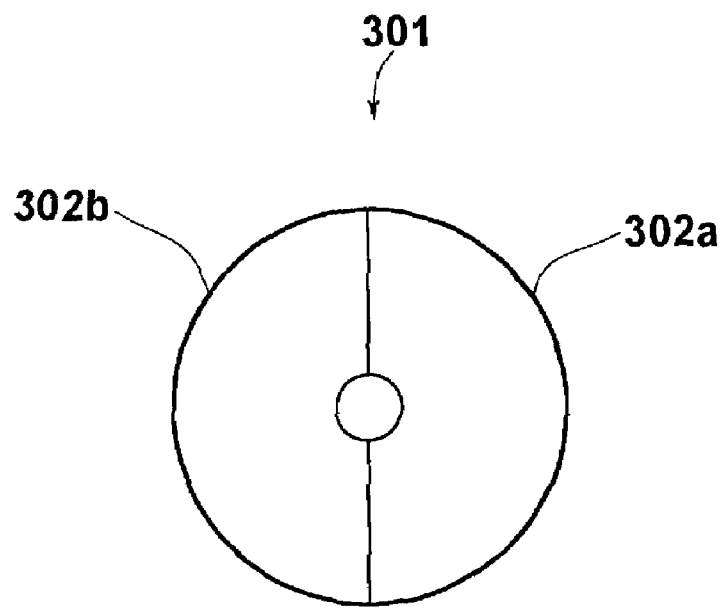
FIG. 4 is a view showing the variable stimulating light cut filter means employed in the fluorescence endoscope of the first embodiment.

As shown in FIG. 4, the variable stimulating light cut filter means 301 comprises an optical filter 302a which cuts light of a wavelength not longer than 420 nm and another optical filter. 302b which cuts light of a wavelength not longer than 510 nm. The optical filter 302a is used when the stimulating light Le1 of 410 nm is projected onto the object part 1 in the fluorescence diagnosis mode to cut the stimulating light Le1 and the optical filter 302b is used when the stimulating light Le2 of 500 nm is projected onto the object part 1 in the disturbance judgment mode to cut the stimulating light Le2. The controller 60 controls the variable stimulating light cut filter means 301 by way of the filter drive system 303 so that the optical filter 302a is inserted into the optical path when the fluorescence diagnosis mode is selected and the optical filter 302b is inserted into the optical path when the disturbance judgment mode is selected.

Figure 5:
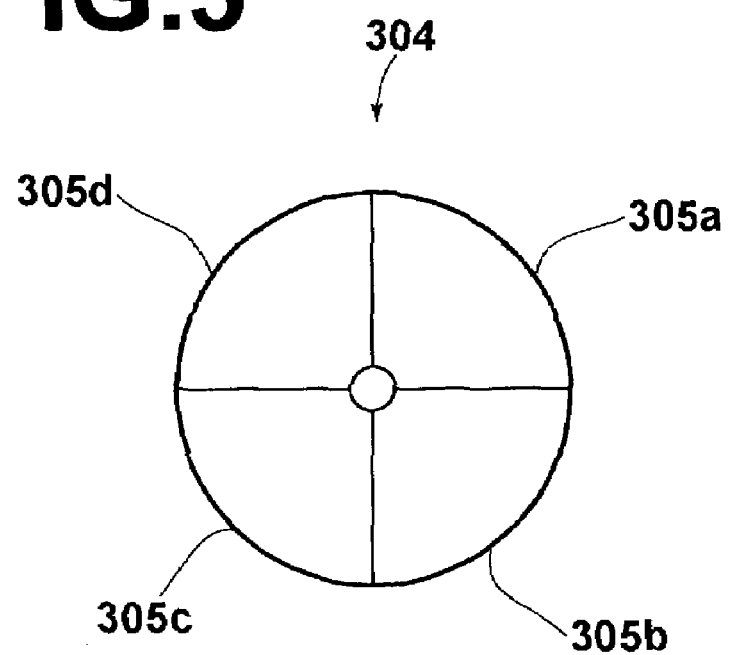
FIG. 5 is a view showing the variable filter means employed in the fluorescence endoscope of the first embodiment.

As shown in FIG. 5, the variable filter means 304 comprises an optical filter 305a which transmits light in a wavelength band from 430 nm to 700 nm, an optical filter 305b which transmits light in a wavelength band from 530 nm to 570 nm, an optical filter 305c which transmits light in a wavelength band from 530 nm to 800 nm, and an optical filter 305d which transmits light in the entire wavelength band. The optical filter 305a is for obtaining the broad-band fluorescence image data (Le1). The optical filters 305b and 305c are respectively for obtaining the narrow-band fluorescence image data (Le2) and the broad-band fluorescence image data (Le2), and the optical filter 305d is for obtaining the IR reflection image data. The controller 60 controls the variable filter means 304 by way of the filter drive system 306 so that the optical filter 305a is inserted into the optical path when the fluorescence diagnosis mode is selected and the stimulating light Le1 is projected onto the object part 1, the optical filters 305b and 305c are alternately inserted into the optical path when the disturbance judgment mode is selected and the stimulating light Le2 is projected onto the object part 1, and the optical filter 305d is inserted into the optical path when the reference light Ls is projected onto the object part 1.

The fluorescence image processing unit 40 comprises a signal processing circuit 401 which processes the signal obtained by the CCD image taking device 308 to obtain an image signal; an A/D convertor 402 which digitizes the image signal obtained by the signal processing circuit 401; an image memory 403 which stores in different storage areas the broad-band fluorescence image data (Le1) representing the fluorescence image Zj1, the narrow-band fluorescence image data (Le2) and the broad-band fluorescence image data (Le2) which represent the fluorescence image Zj2, and the IR reflection image data representing the IR reflection image Zs; a fluorescence yield calculating section 404 which, in the fluorescence diagnosis mode, calculates the yield of fluorescence (Le1) as the first characteristic value by dividing the value of each pixel of the broad-band fluorescence image data (Le1) by the value of the corresponding pixel of the IR reflection image data; a fluorescence diagnostic image generating section 405 which allocates to the pixels color information on the basis of the yield of fluorescence (Le1), allocates to the pixels brightness information on the basis of the value of the IR reflection image data, generates fluorescence diagnostic image data (the first fluorescence diagnostic information) on the basis of combination of the color information and the brightness information and outputs the fluorescence diagnostic image data to a video signal processing circuit 409 to be described later; a fluorescence intensity calculating section 406 which, in the disturbance judgment mode, calculates the normalized intensity of fluorescence (Le2) as the second characteristic value by dividing the value of each pixel of the narrow-band fluorescence image data (Le2) by the value of the corresponding pixel of the broad-band fluorescence image data (Le2); a storage section 407 which stores as the reference values an average Av2 and a standard deviation St2 of the normalized intensities of fluorescences (Le2) obtained in advance from a plurality of clean organic tissues; a disturbance image generating section 408 which calculates the degree of influence B1 of the disturbance factor on the basis of the normalized intensity of fluorescence (Le2) and the reference values, allocates to the pixels color information on the basis of the degree of influence B1, allocates to the pixels brightness information on the basis of the value of the IR reflection image data, generates disturbance judgment image data (the fluorescence diagnostic information) on the basis of combination of the color information and the brightness information and outputs the disturbance judgment image data to the video signal processing circuit 409; and the video signal processing circuit 409 which converts the fluorescence diagnostic image or the disturbance judgment image data to a video signal and outputs the video signal to the monitor 70. The controller 60 is connected to each part and controls the timing of operation of the parts.

Operation of this endoscope will be described, hereinbelow. Operation when the fluorescence diagnosis mode is selected will be described first. The fluorescence image Zj1 and the IR reflection image Zs are taken in a time-sharing fashion. For this purpose, the illumination unit 20 emits the first stimulating light Le1 and the reference light Ls in sequence.

When taking a fluorescence image, the power source 202 is operated under the control of a signal from the controller 60 and the Ga—N semiconductor laser 201 radiates a stimulating light Le1 of a wavelength of 410 nm. The stimulating light Le1 enters the light guide 102a through a lens 203, propagates to the front end of the scope section 10, and then is projected onto the object part 1 by the illumination lens 104.

A fluorescence image Zj1 emitted from the object part 1 upon exposure to the stimulating light Le1 is condensed by the condenser lens 105 to enter the image fiber 103. Then the fluorescence image Zj1 impinges upon the CCD image taking device 308 by way of the image fiber 103, a condenser lens 309, the optical filter 302a of the variable stimulating light cut filter means 301, the optical filter 305a of the variable filter means 304 and a condenser lens 307. The optical filter 302a of the variable stimulating light cut filter means 301 cuts wavelengths not longer than 420 nm and the optical filter 305a of the variable filter means 304 only transmits wavelengths of 430 nm to 700 nm.

Accordingly, the components of the fluorescence image Zj1 in the wavelength band of 430 nm to 700 nm impinges upon the CCD image taking device 308. The fluorescence image in the wavelength band of 430 nm to 700 nm is photoelectrically converted into an electric image signal. The electric image signal is processed by the signal processing circuit 401 and broad-band fluorescence image data (Le1) is output. The broad-band fluorescence image data (Le1) is digitized by the A/D convertor 402 and is stored in the image memory 403 in the storage area therefor.

In substantially the same manner, an IR reflection image Zs formed by the reference light Ls reflected by the object part 1 impinges upon the CCD image taking device 308 by way of the image fiber 103, the condenser lens 309, the optical filter 302a of the variable stimulating light cut filter means 301, the optical filter 305d of the variable filter means 304 and the condenser lens 307. The IR reflection image is photoelectrically converted into an electric image signal. The electric image signal is processed by the signal processing circuit 401 and IR reflection image data is output.

The IR reflection image data is digitized by the A/D convertor 402 and is stored in the image memory 403 in the storage area therefor.

When the broad-band fluorescence image data (Le1) and the IR reflection image data are stored in the image memory 403, the fluorescence yield calculating section 404 calculates the yield of fluorescence (Le1) by dividing the value of each pixel of the broad-band fluorescence image data (Le1) by the value of the corresponding pixel of the IR reflection image data and the fluorescence diagnostic image generating section 405 allocates to the pixels color information on the basis of the yield of fluorescence (Le1), allocates to the pixels brightness information on the basis of the value of the IR reflection image data, generates fluorescence diagnostic image data on the basis of combination of the color information and the brightness information and outputs the fluorescence diagnostic image data to a video signal processing circuit 409. The video signal processing circuit 409 converts the fluorescence diagnostic image to a video signal and outputs the video signal to the monitor 70. The fluorescence diagnostic image which is a pseudo-color image is displayed by the monitor 70.

The fluorescence diagnostic image is displayed in pseudo-color whose hue varies according to the yield of fluorescence (Le1) and whose brightness varies according to the value of the IR reflection image data. Generally, fluorescence emitted from a clean normal tissue is large in the yield and fluorescence emitted from a clean diseased tissue is small in the yield. Accordingly, by setting the pseudo-color to represent the yield of fluorescence, for instance, by allocating pseudo-color to the pixels so that the color of the pixels varies from green to red as the yield of fluorescence decreases, whether the object part 1 is a tissue which emits fluorescence in a large yield (a clean normal tissue or an unclean tissue stained with disturbance factors which emits fluorescence in a yield similar to a normal tissue) or a tissue which emits fluorescence in a small yield (a clean diseased tissue or an unclean tissue stained with disturbance factors which emits fluorescence in a yield similar to a diseased tissue) can be easily seen from the fluorescence diagnostic image. Further since the brightness of each pixel varies according to the intensity of the signal representing the IR reflection image data, protrusions and recesses of the object part 1 and the distance of the object part 1 from the end of the endoscope can be seen from the fluorescence diagnostic image.

The viewer moves the scope section 10 viewing the fluorescence diagnostic image. When a part displayed in red appears in the fluorescence diagnostic image and it is impossible to determine whether the part is a clean diseased tissue or an unclean tissue, the viewer manually switches the endoscope to the disturbance judgment mode by the input system 601.

When the disturbance judgment mode is selected will be described first, the fluorescence image Zj2 and the IR reflection image Zs are taken in a time-sharing fashion. For this purpose, the illumination unit 20 emits the stimulating light Le2 and the reference light Ls in sequence.

The Ga—N semiconductor laser 204 radiates a stimulating light Le2 of a wavelength of 500 nm. The stimulating light Le2 enters the light guide 102b through a lens 206, propagates to the front end of the scope section 10, and then is projected onto the object part 1 by the illumination lens 104.

A fluorescence image Zj2 emitted from the object part 1 upon exposure to the stimulating light Le2 is condensed by the condenser lens 105 to enter the image fiber 103. Then the fluorescence image Zj2 impinges upon the CCD image taking device 308 by way of the image fiber 103, the condenser lens 309, the optical filter 302b of the variable stimulating light cut filter means 301, the optical filter 305b of the variable filter means 304 and the condenser lens 307. The optical filter 302b of the variable stimulating light cut filter means 301 cuts wavelengths not longer than 510 nm and the optical filter 305b of the variable filter means 304 only transmits wavelengths of 530 nm to 570 nm.

Accordingly, the components of the fluorescence image Zj2 in the wavelength band of 530 nm to 570 nm impinges upon the CCD image taking device 308.

The fluorescence image in the wavelength band of 530 nm to 570 nm is photoelectrically converted into an electric image signal. The electric image signal is processed by the signal processing circuit 401 and narrow-band fluorescence image data (Le2) is output. The narrow-band fluorescence image data (Le2) is digitized by the A/D convertor 402 and is stored in the image memory 403 in the storage area therefor.

Thereafter the Ga—N semiconductor laser 204 radiates a stimulating light Le2 of a wavelength of 500 nm. The stimulating light Le2 enters the light guide 102b through a lens 206, propagates to the front end of the scope section 10, and then is projected onto the object part 1 by the illumination lens 104. A fluorescence image Zj2 emitted from the object part 1 upon exposure to the stimulating light Le2 is condensed by the condenser lens 105 to enter the image fiber 103. Then the fluorescence image Zj2 impinges upon the CCD image taking device 308 by way of the image fiber 103, the condenser lens 309, the optical filter 302b of the variable stimulating light cut filter means 301, the optical filter 305c of the variable filter means 304 and the condenser lens 307. The optical filter 302b of the variable stimulating light cut filter means 301 cuts wavelengths not longer than 510 nm and the optical filter 305c of the variable filter means 304 only transmits wavelengths of 530 nm to 800 nm. Accordingly, the components of the fluorescence image Zj2 in the wavelength band of 530 nm to 800 nm impinges upon the CCD image taking device 308.

The fluorescence image in the wavelength band of 530 nm to 800 nm is photoelectrically converted into an electric image signal. The electric image signal is processed by the signal processing circuit 401 and broad-band fluorescence image data (Le2) is output. The broad-band fluorescence image data (Le2) is digitized by the A/D convertor 402 and is stored in the image memory 403 in the storage area therefor.

As in the fluorescence diagnosis mode, an IR reflection image Zs formed by the reference light Ls reflected by the object part 1 impinges upon the CCD image taking device 308 by way of the image fiber 103, the condenser lens 309, the optical filter 302a of the variable stimulating light cut filter means 301, the optical filter 305d of the variable filter means 304 and the condenser lens 307. The IR reflection image is photoelectrically converted into an electric image signal. The electric image signal is processed by the signal processing circuit 401 and IR reflection image data is output. The IR reflection image data is digitized by the A/D convertor 402 and is stored in the image memory 403 in the storage area therefor.

When narrow-band fluorescence image data (Le2), the broad-band fluorescence image data (Le2) and the IR reflection image data are stored in the image memory 403, the fluorescence intensity calculating section 406 calculates the normalized intensity of fluorescence by dividing the value of each pixel of the narrow-band fluorescence image data (Le2) by the value of the broad-band fluorescence image data (Le2). At the same time, the disturbance image generating section 408 calculates the degree of influence B1 of the disturbance factor for each pixel according to the following formula on the basis of the value NF2 of the normalized intensity of fluorescence (Le2) and the average Av2 and the standard deviation St2 of the normalized intensities of fluorescences (Le2) stored in the storage section 407.

$$B1=\{(NF2-Av2)/St2\}^2$$

Then the disturbance image generating section 408 allocates to the pixels color information on the basis of the degree of influence B1 of the disturbance factor (e.g., the disturbance image generating section 408 allocates pseudo-color to the pixels so that the color of the pixels varies from white to magenta as the degree of influence B1 increases), allocates to the pixels brightness information on the basis of the value of the IR reflection image data, generates disturbance judgment image data on the basis of combination of the color information and the brightness information and outputs the disturbance judgment image data to the video signal processing circuit 409. The video signal processing circuit 409 converts the disturbance judgment image data to a video signal and outputs the video signal to the monitor 70. The disturbance judgment image which is a pseudo-color image is displayed by the monitor 70.

The viewer can recognize the part the influence of the disturbance factor on which is significant by viewing the disturbance judgment image. When a part displayed in red in the fluorescence diagnosis image is displayed in white in the disturbance judgment image, the part may be considered to be a clean diseased tissue. Whereas, when a part displayed in red in the fluorescence diagnosis image is displayed in magenta in the disturbance judgment image, the part may be considered to be an unclean tissue.

As can be understood from the description above, when the object part cannot be determined whether it is a clean diseased tissue or an unclean tissue on a fluorescence diagnostic image, the endoscope is switched to the disturbance judgment mode. By viewing a disturbance judgment image, it is possible to determine whether the object part is a clean diseased tissue or an unclean tissue. Accordingly, mistaking an unclean tissue for a clean diseased tissue is suppressed and the tissue-property distinguishing accuracy can be improved.

Though, in the embodiment described above, light of a wavelength of 410 nm is employed as the stimulating light Le1 and light of a wavelength of 500 nm is employed as the stimulating light Le2, the wavelengths of the stimulating light Le1 and Le2 need not be limited to these values so long as the wavelength of the stimulating light Le1 is such that when the stimulating light Le1 is projected onto clean object parts different in properties, different yields of fluorescence are obtained, and the wavelength of the stimulating light Le2 is such that when the stimulating light Le2 is projected onto a clean object part and an unclean object part, different normalized intensities of fluorescence are obtained. For example, light of a wavelength of 360 nm may be employed as the stimulating light Le2.

Figure 6:
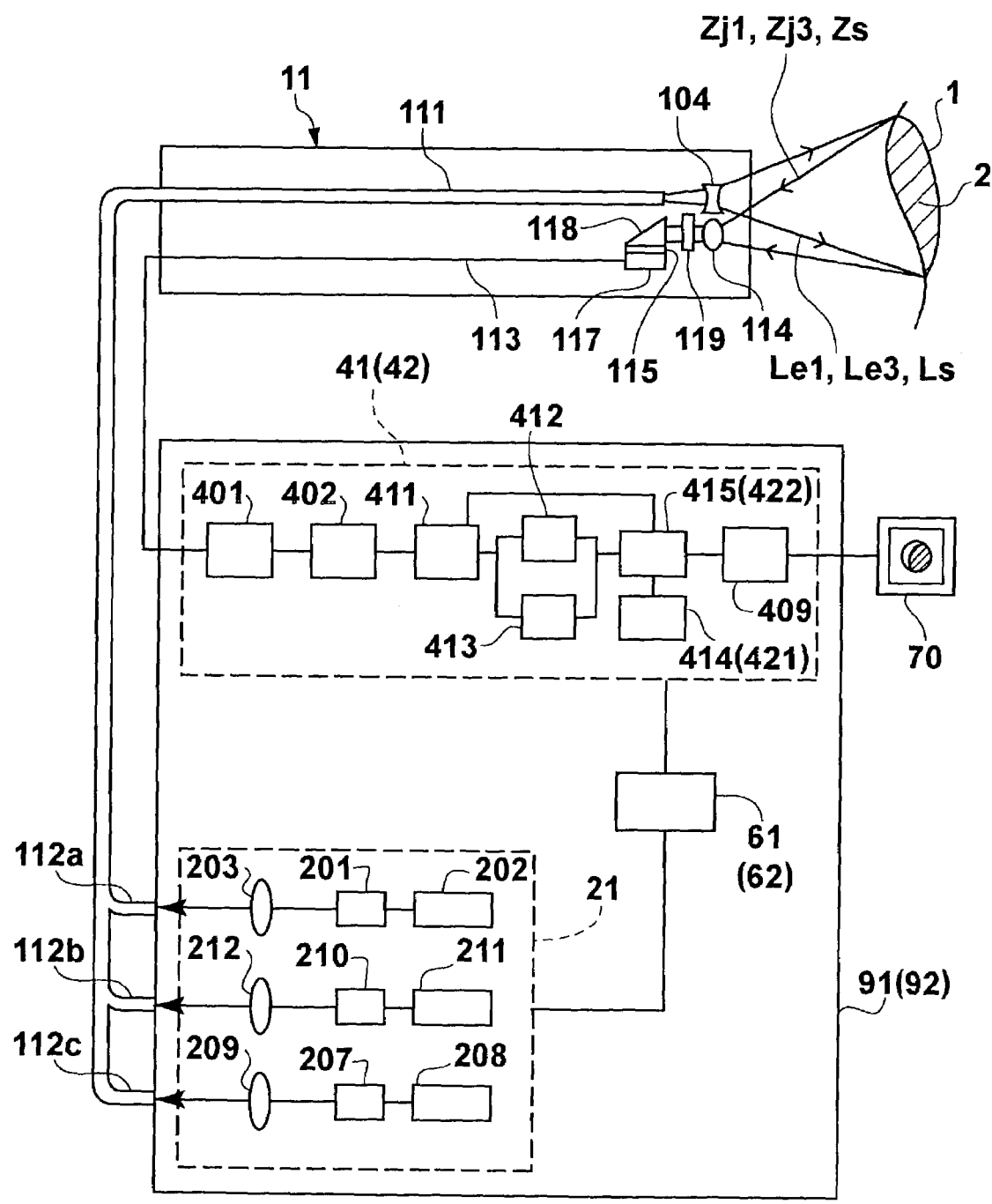
FIG. 6 is a view showing in brief fluorescence endoscopes in accordance with second and third embodiments of the present invention.

A fluorescence endoscope in accordance with a second embodiment of the present invention will be described with reference to FIGS. 6 and 7, hereinbelow.

In the fluorescence endoscope of this embodiment, stimulating light Le1 of a wavelength of 410 nm is projected onto the object part 1, a normalized intensity of fluorescence is obtained on the basis of fluorescence emitted from the object part 1 upon exposure to the stimulating light Le1 (This normalized intensity of fluorescence will be referred to as "the normalized intensity of fluorescence (Le1)", hereinbelow), stimulating light Le3 of a wavelength of 360 nm is projected onto the object part 1, a normalized intensity of fluorescence is obtained on the basis of fluorescence emitted from the object part 1 upon exposure to the stimulating light Le3 (This normalized intensity of fluorescence will be referred to as "the normalized intensity of fluorescence (Le3)", hereinbelow), whether each pixel 2 of the object part 1 is a clean tissue or an unclean tissue is judged on the basis of the normalized intensity of fluorescence (Le1) and the normalized intensity of fluorescence (Le3), color information for each pixel is generated on the basis of the result of the judgment, IR reflection image data is obtained on the basis of reflected reference light Ls (near-infrared light) reflected by the object part 1 when the reference light Ls is projected onto the object part 1, brightness information for each pixel is generated on the basis of the value of the corresponding pixel of the IR reflection image data, and a disturbance judgment/fluorescence diagnostic image (a pseudo-color image) is displayed on the monitor 70 on the basis of combination of the color information and the brightness information.

The fluorescence endoscope of this embodiment comprises a scope section 11 which is inserted into a suspected diseased part of a patient, an illumination unit 21 provided with sources of the stimulating light Le1, the stimulating light Le3, and the reference light Ls, a fluorescence image processing unit 41, a controller 61 which is connected to the units and controls the timing of operation of the units, and a monitor 70 which displays a disturbance judgment/fluorescence diagnostic image as a visible image. The fluorescence image processing unit 41 generates color information for each pixel on the basis of the result of the judgment of whether each pixel 2 of the object part 1 is a clean tissue or an unclean tissue on the basis of the normalized intensity of fluorescence (Le1) and the normalized intensity of fluorescence (Le3) and brightness information for each pixel on the basis of the value of the corresponding pixel of the IR reflection image data, and outputs a video signal representing the disturbance judgment/fluorescence diagnostic image on the basis of both the color information and the brightness information.

The illumination unit 21, the fluorescence image processing unit 41 and the controller 61 form a processor section 91. The scope section 11 and the processor section 91 are connected by way of a connector (not shown) and the processor section 91 and the monitor 70 are connected by way of a connector (not shown).

A light guide 111 and a CCD cable 113 extend inside the scope section 11 up to the front end of the endoscope. An illumination lens 104 is provided on the front end of the light guide 111, and an objective lens 114 is provided on the front end of the CCD cable 113. A CCD image taking device 117 provided with a mosaic filter 115 comprising a number of fine band-pass filters arranged in a mosaic pattern is connected to the end of the CCD cable 113, and a prism 118 is mounted on the CCD image taking device 117. A stimulating light cut filter 119 which cuts wavelengths not longer than 420 nm is disposed between the prism 118 and the objective lens 114.

The light guide 111 comprises a light guide 112a for guiding the stimulating light Le1, a light guide 112b for guiding the stimulating light Le3, and a light guide 112c for guiding the reference light Ls which are bundled together and integrated into a cable. The light guides 112a to 112c are connected to the illumination unit 21 and the image fiber 113 is connected to the fluorescence image processing unit 41 at its one end.

Figure 7:
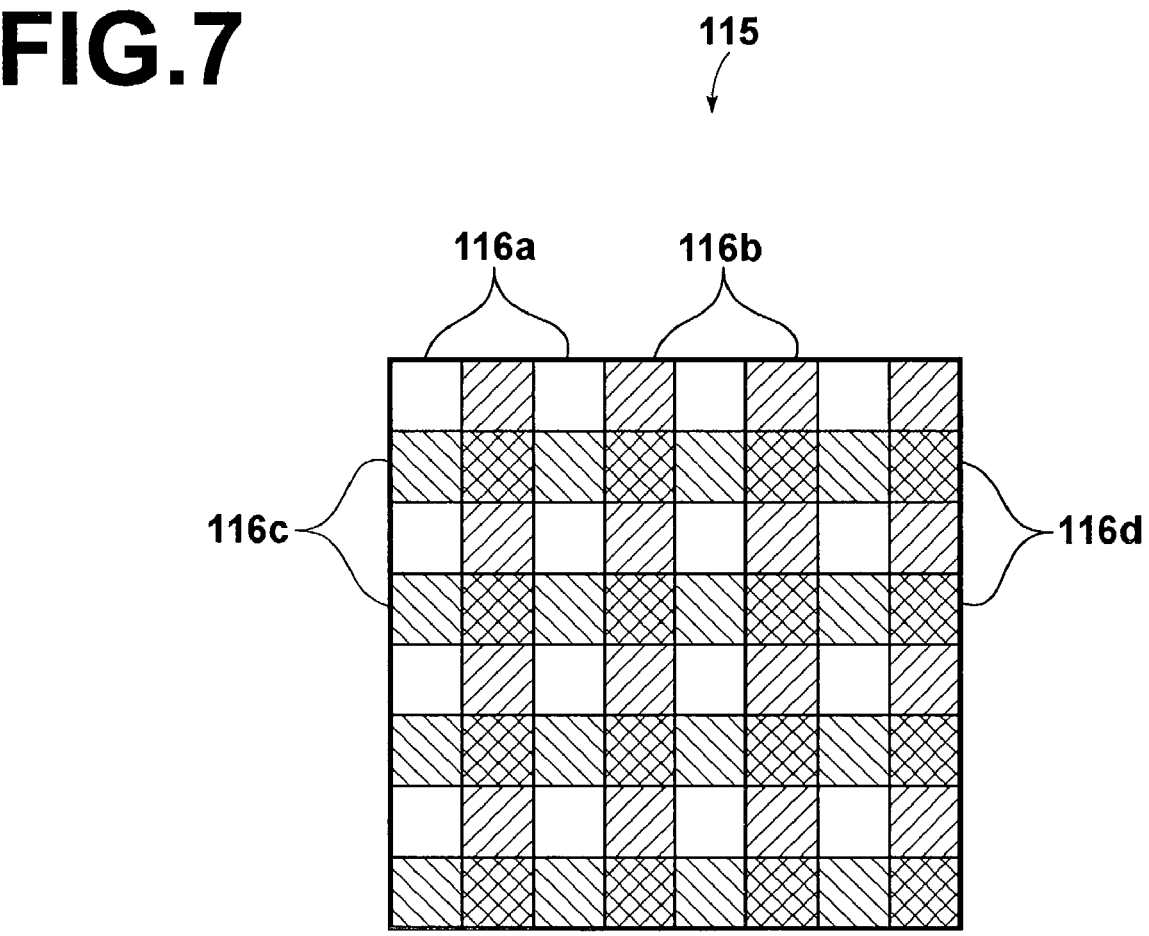
FIG. 7 is a view showing the mosaic filter employed in the fluorescence endoscope of the second and third embodiments.

As shown in FIG. 7, the mosaic filter 115 comprises a plurality of fine optical filters 116a each being a band-pass filter transmitting light in a wavelength band of 430 nm to 530 nm, a plurality of fine optical filters 116b each being a band-pass filter transmitting light in a wavelength band of 430 nm to 490 nm, a plurality of fine optical filters 116c each being a band-pass filter transmitting light in a wavelength band of 430 nm to 700 nm, and a plurality of fine optical filters 116d each transmitting light in the entire wavelength band, which are arranged in a mosaic pattern. Each optical filter is in one-to-one correspondence with a pixel of the CCD image taking device 117. The optical filter 116a is for obtaining narrow-band fluorescence image data with the stimulating light Le1 projected onto the object part 1, the optical filter 116b is for obtaining narrow-band fluorescence image data with the stimulating light Le3 projected onto the object part 1, the optical filter 116c is for obtaining broad-band fluorescence image data with the stimulating light Le1 and the stimulating light Le3 projected onto the object part 1 and the optical filter 116d is for obtaining the IR reflection image data.

The illumination unit 21 comprises a stimulating light source unit comprising a Ga—N semiconductor laser 201 which emits the stimulating light Le1 of a wavelength of 410 nm and a power source 202 for the semiconductor laser 201, a stimulating light source unit comprising a Ga—N semiconductor laser 210 which emits the stimulating light Le3 of a wavelength of 360 nm and a power source 211 for the semiconductor laser 204, and a reference light source unit comprising a reference light source 207 which emits the reference light Ls and a power source 208 for the reference light source 207.

The fluorescence image processing unit 41 comprises a signal processing circuit 401 which processes the signal obtained by the CCD image taking device 117 to obtain image data; an A/D convertor 402 which digitizes the image data output from the signal processing circuit 401; an image memory 411 which stores in different storage areas narrow-band fluorescence image data (Le1) and broad-band fluorescence image data (Le1) which are respectively obtained through pixels of the CCD image taking device 117 corresponding to the optical filters 116a and 116c of the mosaic filter 115 when the stimulating light Le1 is projected onto the object part 1, narrow-band fluorescence image data (Le3) and broad-band fluorescence image data (Le3) which are respectively obtained through pixels of the CCD image taking device 117 corresponding to the optical filters 116b and 116c of the mosaic filter 115 when the stimulating light Le3 is projected onto the object part 1, and the IR reflection image data obtained through pixels of the CCD image taking device 117 corresponding to the optical filters 116d of the mosaic filter 115 when the reference light Ls is projected onto the object part 1; a fluorescence intensity calculating section 412 which calculates the normalized intensity of fluorescence (Le1) as the first characteristic value by dividing the value of each pixel of the narrow-band fluorescence image data (Le1) by the value of the adjacent pixel of the broad-band fluorescence image data (Le1), the narrow-band fluorescence image data (Le1) and the broad-band fluorescence image data (Le1) being stored in the image memory 411; a fluorescence intensity calculating section 413 which calculates the normalized intensity of fluorescence (Le3) as the second characteristic value by dividing the value of each pixel of the narrow-band fluorescence image data (Le3) by the value of the adjacent pixel of the broad-band fluorescence image data (Le3), the narrow-band fluorescence image data (Le3) and the broad-band fluorescence image data (Le3) being stored in the image memory 411; a storage section 414 which stores as the reference values an average Av3 and a standard deviation St3 of the normalized intensities of fluorescences (Le3) obtained in advance from a plurality of clean organic tissues; a fluorescence diagnostic image generating section 415 which generates color information for each pixel on the basis of the result of the judgment of whether each pixel 2 of the object part 1 is a clean tissue or an unclean tissue on the basis of the normalized intensities of fluorescence (Le1) and fluorescence (Le3) calculated by the fluorescence intensity calculating section 412 and the fluorescence intensity calculating section 413 and the reference values stored in the storage section 414, generates brightness information for each pixel on the basis of the value of the corresponding pixel of the IR reflection image data stored in the image memory 411, and generates disturbance judgment/fluorescence diagnostic image data on the basis of combination of the color information and the brightness information; and a video signal processing circuit 409 which converts the disturbance judgment/fluorescence diagnostic image data to a video signal and outputs the video signal to the monitor 70. The controller 60 is connected to each part and controls the timing of operation of the parts.

Operation of this endoscope will be described, hereinbelow. A fluorescence image Zj1 (a fluorescence image formed by fluorescence emitted from the object part 1 upon exposure to the stimulating light Le1), a fluorescence image Zj3 (a fluorescence image formed by fluorescence emitted from the object part 1 upon exposure to the stimulating light Le3) and an IR reflection image Zs (an image formed by reflected reference light Ls) are taken in a time-sharing fashion.

The power source 202 is operated under the control of a signal from the controller 61 and the Ga—N semiconductor laser 201 radiates a stimulating light Le1 of a wavelength of 410 nm. The stimulating light Le1 enters the light guide 112a through a lens 203, propagates to the front end of the scope section 11, and then is projected onto the object part 1 by the illumination lens 104.

Fluorescence emitted from the object part 1 upon exposure to the stimulating light Le1 is condensed by the condenser lens 114 and focused on the CCD image taking device 117 as the fluorescence image Zj1 by way of the stimulating light cut filter 119, the prism 118 and the mosaic filter 115. The stimulating light cut filter 119 cuts wavelengths not longer than 420 nm and accordingly the reflected stimulating light Le1 is prevented from impinging upon the CCD image taking device 117. The CCD image taking device 117 photoelectrically converts the fluorescence image Zj1 into an image signal.

The image signal output from the CCD image taking device 117 is processed by the signal processing circuit 401, is digitized by the A/D convertor 402 and is stored in the image memory 411 divided into the narrow-band fluorescence image data (Le1) obtained through the optical filters 116a and the broad-band fluorescence image data (Le1) obtained through the optical filters 116c.

Then the power source 212 is operated under the control of a signal from the controller 61 and the Ga—N semiconductor laser 211 radiates a stimulating light Le3 of a wavelength of 360 nm. The stimulating light Le3 enters the light guide 112b through a lens 213, propagates to the front end of the scope section 11, and then is projected onto the object part 1 by the illumination lens 104.

Fluorescence emitted from the object part 1 upon exposure to the stimulating light Le3 is imaged on the CCD image taking device 117 as the fluorescence image Zj3 by way of the mosaic filter 115. The CCD image taking device 117 photoelectrically converts the fluorescence image Zj3 into an image signal. The image signal output from the CCD image taking device 117 is processed by the signal processing circuit 401, is digitized by the A/D convertor 402 and is stored in the image memory 411 divided into the narrow-band fluorescence image data (Le3) obtained through the optical filters 116b and the broad-band fluorescence image data (Le3) obtained through the optical filters 116c.

Taking the IR reflection image Zs will be described, hereinbelow. The power source 208 is operated under the control of a signal from the controller 61 and the reference light source 207 radiates near-infrared light as the reference light Ls. The reference light Ls enters the light guide 112c through a lens 209, propagates to the front end of the scope section 11, and then is projected onto the object part 1 by the illumination lens 104.

The reflected reference light Ls reflected by the object part 1 is condensed by the condenser lens 114 and focused on the CCD image taking device 117 as the IR reflection image Zs by way of the prism 118 and the mosaic filter 115. The CCD image taking device 117 photoelectrically converts the IR reflection image Zs into an image signal. The image signal output from the CCD image taking device 117 is processed by the signal processing circuit 401 and is digitized by the A/D convertor 402. Image data representing the light passing through the optical filters 116d is stored in the image memory 411 as the IR reflection image data.

When the narrow-band fluorescence image data (Le1), the broad-band fluorescence image data (Le1), the narrow-band fluorescence image data (Le3), the broad-band fluorescence image data (Le3), and the IR reflection image data are stored in the image memory 411, the fluorescence intensity calculating section 412 calculates the normalized intensity of fluorescence (Le1) by dividing the value of each pixel of the narrow-band fluorescence image data (Le1) stored in the image memory 411 by the value of the adjacent pixel of the broad-band fluorescence image data (Le1) stored in the image memory 411. Further, the fluorescence intensity calculating section 413 calculates the normalized intensity of fluorescence (Le3) by dividing the value of each pixel of the narrow-band fluorescence image data (Le3) stored in the image memory 411 by the value of the adjacent pixel of the broad-band fluorescence image data (Le3) stored in the image memory 411.

The fluorescence diagnostic image generating section 415 generates color information to the pixels on the basis of the normalized intensities of fluorescence (Le1). Generally, the normalized intensity of fluorescence emitted from a normal tissue is large and the normalized intensity of fluorescence emitted from a diseased tissue is small. Accordingly, by setting the pseudo-color to represent the normalized intensity of fluorescence, for instance, by allocating pseudo-color to the pixels so that the color of the pixels varies from green to red as the normalized intensity of fluorescence decreases, whether the object part 1 is a normal tissue or a diseased tissue can be easily seen from the fluorescence diagnostic image.

At the same time, the fluorescence diagnostic image generating section 415 determines whether each pixel 2 of the object part 1 is a clean tissue or an unclean tissue on the basis of the value NF3 of the normalized intensity of fluorescence (Le3) and the average Av3 and the standard deviation St3 of the normalized intensities of fluorescences (Le3) which have been obtained from a plurality of clean tissues and stored in the storage section 414. That is, when the value NF3 of the normalized intensity of fluorescence (Le3) satisfies the following formula, it is determined that the pixel 2 is a clean tissue, whereas when the value NF3 of the normalized intensity of fluorescence (Le3) does not satisfy the following formula, it is determined that the pixel 2 is an unclean tissue.

$$Av3-St3<NF3<Av3+St3$$

When it is determined that a pixel is an unclean tissue, magenta is allocated to the pixel in place of color which varies from green to red as the normalized intensity of fluorescence decreases.

Further, the fluorescence diagnostic image generating section 415 generates brightness information on the basis of the value of the IR reflection image data, generates disturbance judgment/fluorescence diagnostic image data on the basis of combination of the color information and the brightness information and outputs the disturbance judgment/fluorescence diagnostic image data to the video signal processing circuit 409. The video signal processing circuit 409 converts the disturbance judgment/fluorescence diagnostic image data to a video signal and outputs the video signal to the monitor 70. The disturbance judgment/fluorescence diagnostic image which is a pseudo-color image is displayed by the monitor 70.

As can be understood from the description above, by viewing the disturbance judgment/fluorescence diagnostic image, it is possible to determine whether the object part is a clean tissue or an unclean tissue and it is possible to determine whether the object part is a clean normal tissue or a clean diseased tissue on the basis of the color of the object part which varies from green to red. Accordingly, mistaking an unclean tissue for a clean diseased tissue is suppressed and the tissue-property distinguishing accuracy can be improved.

A fluorescence endoscope in accordance with a third embodiment of the present invention will be described, hereinbelow. The fluorescence endoscope of the third embodiment is substantially the same as the second embodiment shown in FIG. 6, and accordingly the elements different from those in the second embodiment are given different reference numerals in brackets in FIG. 6. Whereas, elements analogous to those shown in FIG. 6 are given the same reference numerals and will not be described unless necessary.

In this embodiment, white is allocated to pixels which are not smaller than a predetermined value in normalized intensity of fluorescence (Le1) and at the same time are out of a predetermined range in normalized intensity of fluorescence (Le3), green is allocated to pixels which are not smaller than the predetermined value in normalized intensity of fluorescence (Le1) and at the same time are within the predetermined range in normalized intensity of fluorescence (Le3), red is allocated to pixels which are smaller than the predetermined value in normalized intensity of fluorescence (Le1) and at the same time are within the predetermined range in normalized intensity of fluorescence (Le3), and magenta is allocated to pixels which are smaller than the predetermined value in normalized intensity of fluorescence (Le1) and at the same time are out of the predetermined range in normalized intensity of fluorescence (Le3).

In this embodiment, the fluorescence image processing unit 42 comprises a signal processing circuit 401; an A/D convertor 402; an image memory 411; a fluorescence intensity calculating section 412 which calculates the normalized intensity of fluorescence (Le1); a fluorescence intensity calculating section 413 which calculates the normalized intensity of fluorescence (Le3); a storage section 421 which stores a threshold value S1 which has been set on the basis of the normalized intensities of fluorescence (Le1) obtained in advance from a plurality of clean normal tissues and the normalized intensities of fluorescence (Le1) obtained in advance from a plurality of clean diseased tissues and an average Av3 and a standard deviation St3 of the normalized intensities of fluorescences (Le3) obtained in advance from a plurality of clean organic tissues; a fluorescence diagnostic image generating section 422 which generates color information for each pixel on the basis of the normalized intensities of fluorescence (Le1) and fluorescence (Le3) calculated by the fluorescence intensity calculating section 412 and the fluorescence intensity calculating section 413 and the threshold value S1, the average Av3 and the standard deviation stored in the storage section 421, generates brightness information for each pixel on the basis of the value of the corresponding pixel of the IR reflection image data stored in the image memory 411, and generates disturbance judgment/fluorescence diagnostic image data on the basis of combination of the color information and the brightness information; and a video signal processing circuit 409.

When the normalized intensity of fluorescence (Le1) and the normalized intensity of fluorescence (Le3) are calculated, the fluorescence diagnostic image generating section 422 determines whether the value NF1 of the normalized intensity of fluorescence (Le1) of each pixel 2 of the object part 1 is not smaller than the threshold value S1. Then the fluorescence diagnostic image generating section 422 determines whether each pixel 2 of the object part 1 is a clean tissue or an unclean tissue on the basis of the value NF3 of the normalized intensity of fluorescence (Le3) and the average Av3 and the standard deviation St3 of the normalized intensities of fluorescences (Le3) which have been obtained from a plurality of clean tissues and stored in the storage section 421. That is, when the value NF3 of the normalized intensity of fluorescence (Le3) satisfies the following formula, it is determined that the pixel 2 is a clean tissue.

$$Av3-St3<NF3<Av3+St3$$

White is allocated to a pixel when the value NF1 is not smaller than the threshold value S1 and at the same time the value NF3 does not satisfy the above formula, green is allocated to a pixel when the value NF1 is not smaller than the threshold value S1 and at the same time the value NF3 satisfies the above formula, red is allocated to a pixel when the value NF1 is smaller than the threshold value S1 and at the same time the value NF3 satisfies the above formula, and magenta is allocated to a pixel when the value NF1 is smaller than the threshold value S1 and at the same time the value NF3 does not satisfy the above formula. Further, the fluorescence diagnostic image generating section 415 generates brightness information on the basis of the value of the IR reflection image data, generates disturbance judgment/fluorescence diagnostic image data on the basis of combination of the color information and the brightness information and outputs the disturbance judgment/fluorescence diagnostic image data to the video signal processing circuit 409. The video signal processing circuit 409 converts the disturbance judgment/fluorescence diagnostic image data to a video signal and outputs the video signal to the monitor 70. The disturbance judgment/fluorescence diagnostic image which is a pseudo-color image is displayed by the monitor 70.

As can be understood from the description above, by viewing the disturbance judgment/fluorescence diagnostic image, it is possible to determine whether the object part is a clean normal tissue (displayed in green), a clean diseased tissue (displayed in red), an unclean tissue stained with a disturbance factor (displayed in white) which emits, upon exposure to the stimulating light Le1, fluorescence which resembles in shape of spectrum fluorescence emitted from a normal tissue or an unclean tissue stained with a disturbance factor (displayed in magenta) which emits, upon exposure to the stimulating light Le1, fluorescence which resembles in shape of spectrum fluorescence emitted from a diseased tissue. Accordingly, mistaking an unclean tissue for a clean diseased tissue is suppressed and the tissue-property distinguishing accuracy can be improved.

Further, whether each pixel 2 of the object part is a clean normal tissue, a clean diseased tissue, an unclean tissue stained with a disturbance factor which emits, upon exposure to the stimulating light Le1, fluorescence which resembles in shape of spectrum fluorescence emitted from a normal tissue or an unclean tissue stained with a disturbance factor which emits, upon exposure to the stimulating light Le1, fluorescence which resembles in shape of spectrum fluorescence emitted from a diseased tissue upon exposure to the stimulating light Le1 is judged and the result of the judgment is displayed in different colors. Accordingly the result of the judgment can be easily recognized.

Though, in the endoscopes of the above embodiments, a fluorescence diagnostic image is only displayed, the endoscopes may be arranged to display also an ordinary color image.

Though, in the endoscopes of the second and third embodiments, a single color, i.e., white or magenta, is allocated to a pixel which is determined to be an unclean tissue, the degree of influence B2 of the disturbance factor for each pixel may be calculated according to the following formula in the same manner as the degree of influence B1 in the first embodiment and color information may be allocated to each pixel so that the color of the pixels varies on the basis of the degree of influence B2 of the disturbance factor.

$$B2=\{(NF3-Av3)/St3\}^2$$

Though, in the second and third embodiments, the mosaic filter 115 comprises optical filters 116a transmitting light in a wavelength band of 430 nm to 530 nm, optical filters 116b transmitting light in a wavelength band of 430 nm to 490 nm, optical filters 116c transmitting light in a wavelength band of 430 nm to 700 nm, and optical filters 116d transmitting light in the entire wavelength band, the optical filters transmitting light in a wavelength band of 430 nm to 530 nm may be caused to double as the optical filters transmitting light in a wavelength band of 430 nm to 490 nm and the optical filters transmitting light in the entire wavelength band may be caused to double as the optical filters transmitting light in a wavelength band of 430 nm to 700 nm. In this case, the mosaic filter may comprise only two kinds of optical filters, which results in improvement of resolution and increase in amount of detected fluorescence.

The clean diseased tissue may be marked or displayed in a flashing fashion to be more noticeable. Similarly, the unclean tissue may be marked or displayed in a flashing fashion to be more noticeable. Further, it is possible not to display unclean tissues so that only clean tissues are displayed on the monitor. Conversely, only unclean tissues may be displayed on the monitor.

Further, in the endoscopes of the first to third embodiments, it is possible to correct the yield of fluorescence (Le1) or the normalized intensity of fluorescence (Le1) according to the calculated degree of disturbance to a value which would be obtained from a clean tissue and to allocate color on the basis of the corrected yield of fluorescence (Le1) or the corrected normalized intensity of fluorescence (Le1). For example, in the case of the third embodiment, the normalized intensity of fluorescence (Le1) is multiplied by $(1+B2\cdot\alpha)$ ($\alpha$ is a coefficient representing the degree of correction and $0<\alpha\leq1$), color is allocated on the basis of the product.

An endoscope in accordance with a fourth embodiment of the present invention will be described with reference to FIGS. 8 to 11, hereinbelow.

The fluorescence endoscope works in one of an ordinary image mode, a fluorescence diagnosis mode and a disturbance measurement mode which are switched by operation of an input system 631. In the ordinary image mode, an ordinary color image is displayed on the monitor 70. In the fluorescence diagnosis mode, stimulating light Le1 of a wavelength of 410 nm is projected onto an object part 1, and a fluorescence diagnostic image is displayed on a monitor 70, the fluorescence diagnostic image being a pseudo-color image obtained by allocating pseudo-colors on the basis of a normalized intensity of fluorescence (Le1) emitted from the object part 1, and in the disturbance measurement mode, stimulating light Le3 of a wavelength of 360 nm is projected onto the object part 1 through a quartz fiber 53, fluorescence emitted from the object part 1 upon exposure to the stimulating light Le3 is detected through a quartz fiber, the degree of influence of the disturbance factor is calculated on the basis of the normalized intensity of fluorescence (Le3) emitted from the object part 1 and the degree of influence of the disturbance factor is displayed on the monitor 70.

In the ordinary image mode, red light Lr, green light Lg, and blue light Lb are projected onto the object part 1 in sequence, ordinary images formed by the red light Lr, green light Lg, and blue light Lb reflected at the object part 1 are taken by a CCD image taking device 117, and an ordinary color image is displayed on the monitor 70 on the basis of color image data obtained by processing the three color images in an ordinary way.

In the fluorescence diagnosis mode, narrow-band fluorescence image data (Le1) in a wavelength band of 430 nm to 530 nm is obtained on the basis of fluorescence emitted from the object part 1 upon exposure to the stimulating light Le1 of a wavelength of 410 nm, broad-band fluorescence image data (Le1) in a wavelength band of 430 nm to 700 nm is obtained on the basis of fluorescence emitted from the object part 1 upon exposure to the stimulating light Le1 of a wavelength of 410 nm, IR reflection image data is obtained on the basis of reflected reference light Ls (near-infrared light) reflected by the object part 1 when the reference light Ls is projected onto the object part 1, a normalized intensity of fluorescence (Le1) is obtained by dividing the value of each pixel of the narrow-band fluorescence image data (Le1) by the value of the corresponding pixel of the broad-band fluorescence image data (Le1), color information for each pixel is generated on the basis of the normalized intensity of fluorescence (Le1) for the pixel, brightness information for each pixel is generated on the basis of the value of the corresponding pixel of the IR reflection image data, and a fluorescence diagnostic image is displayed on the monitor 70 on the basis of combination of the color information and the brightness information.

In the disturbance measurement mode, a narrow-band fluorescence intensity F1 in a narrow wavelength band of 430 nm to 490 nm is obtained on the basis of fluorescence emitted from each pixel 2 of the object part 1 upon exposure to the stimulating light Le3 of a wavelength of 360 nm, a broad-band fluorescence intensity F2 in a broad wavelength band of 430 nm to 700 nm is obtained on the basis of fluorescence emitted from each pixel 2 of the object part 1 upon exposure to the stimulating light Le3 of a wavelength of 360 nm, the normalized intensity of fluorescence F1/F2 is obtained pixel by pixel by dividing the value of each pixel of the narrow-band fluorescence intensity F1 by the value of the corresponding pixel of the broad-band fluorescence intensity F2, and the degree of influence B3 of the disturbance factor for each pixel 2 is calculated on the basis of the normalized intensity of fluorescence F1/F2 and reference values which have been stored in a storage section 519.

Figure 8:
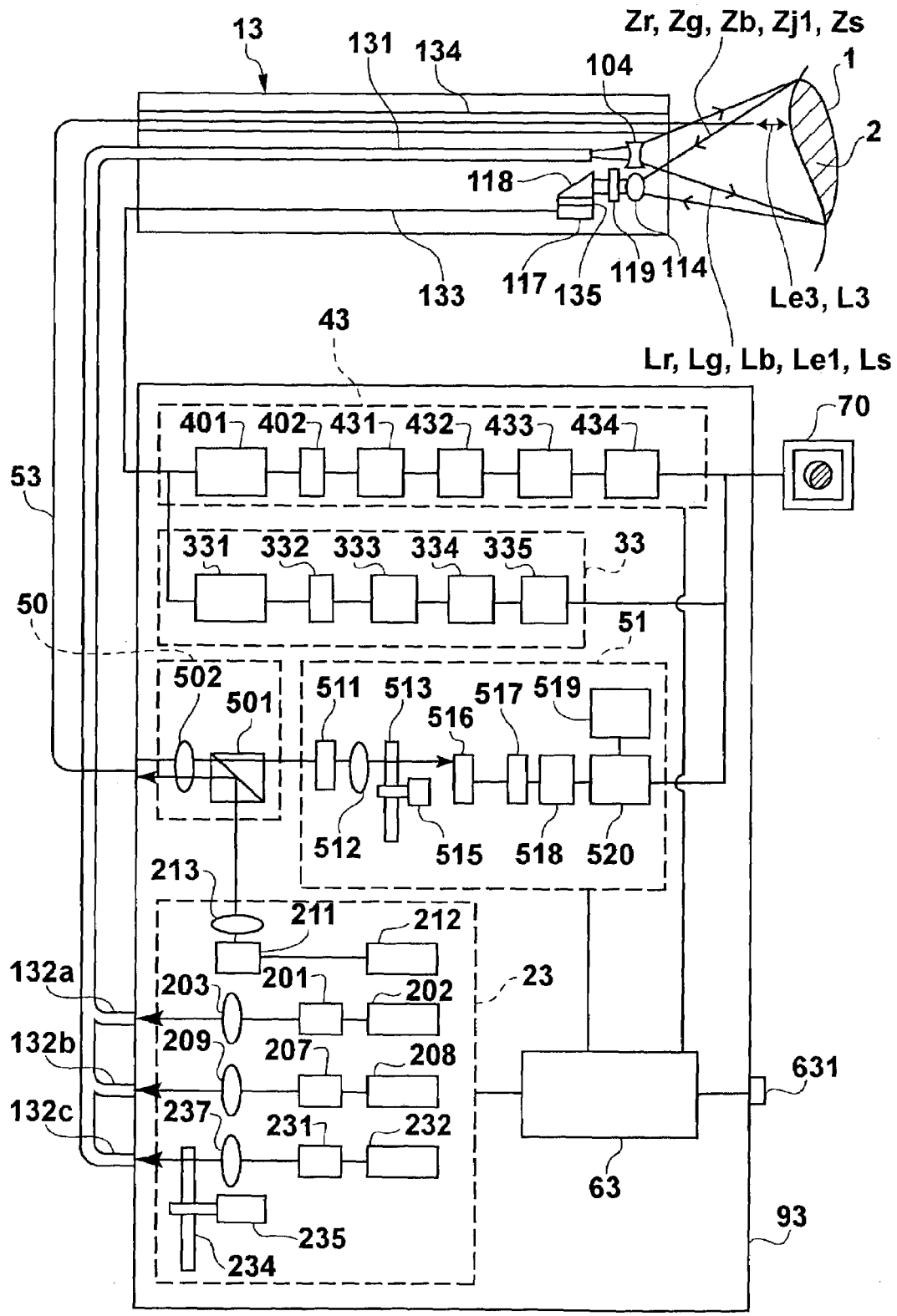
FIG. 8 is a view showing in brief a fluorescence endoscope in accordance with a fourth embodiment of the present invention.

The fluorescence endoscope of the fourth embodiment comprises, as shown in FIG. 8, a scope section 13 which is inserted into a suspected diseased part of a patient, an illumination unit 23 provided with sources of the stimulating light Le1 of a wavelength of 410 nm, the stimulating light Le3 of a wavelength of 360 nm, the reference light Ls, and the red light Lr, green light Lg, and blue light Lb projected onto the object part 1 in sequence in order to take an ordinary color image (will be referred to as "the sequential light", hereinbelow), an ordinary image processing unit 33 which outputs ordinary image data, a fluorescence image processing unit 43 which calculates the normalized intensity of fluorescence (Le1) on the basis of the narrow-band fluorescence image data (Le1) and the broad-band fluorescence image data (Le1) and outputs fluorescence diagnostic image data on the basis of the normalized intensity of fluorescence (Le1) and the IR reflection image data, an optical path separating unit 50 which separates the optical path of the stimulating light Le3 and the optical path of the detected fluorescence, a disturbance calculation unit 51 which outputs the degree of influence B3 of the disturbance factor calculated on the basis of the normalized intensity of fluorescence F1/F2 and reference values which have been stored, a controller 63 which is connected to the units and controls the timing of operation of the units, the input system 631 connected to the controller 63, the monitor 70 and the quartz fiber 53 which propagates the stimulating light Le3 and fluorescence emitted from the pixels 2 of the object part 1 upon exposure to the stimulating light Le3.

The illumination unit 23, the ordinary image processing unit 33, the fluorescence image processing unit 43, the optical path separating unit 50, the disturbance calculation unit 51 and the controller 63 form a processor section 93. The scope section 13 and the processor section 93 are connected by way of a connector (not shown), the quartz fiber 53 and the processor section 93 are connected by way of a connector (not shown) and the processor section 93 and the monitor 70 are connected by way of a connector (not shown).

The scope section 13 is provided with a light guide 131, a CCD cable 133 and a forceps port 134 through which the quartz fiber 53 extends. An illumination lens 104 is provided on the front end of the light guide 131, and an objective lens 114 is provided on the front end of the CCD cable 133. A CCD image taking device 117 provided with a mosaic filter 135 comprising a number of fine band-pass filters arranged in a mosaic pattern is connected to the end of the CCD cable 133, and a prism 118 is mounted on the CCD image taking device 117. A stimulating light cut filter 119 which cuts wavelengths not longer than 420 nm is disposed between the prism 118 and the objective lens 114.

The light guide 131 comprises a light guide 132a for guiding the stimulating light Le1, a light guide 132b for guiding the reference light Ls, and a light guide 132c for guiding the sequential light which are bundled together and integrated into a cable. The light guides 132a to 132c are connected to the illumination unit 23.

Figure 9:
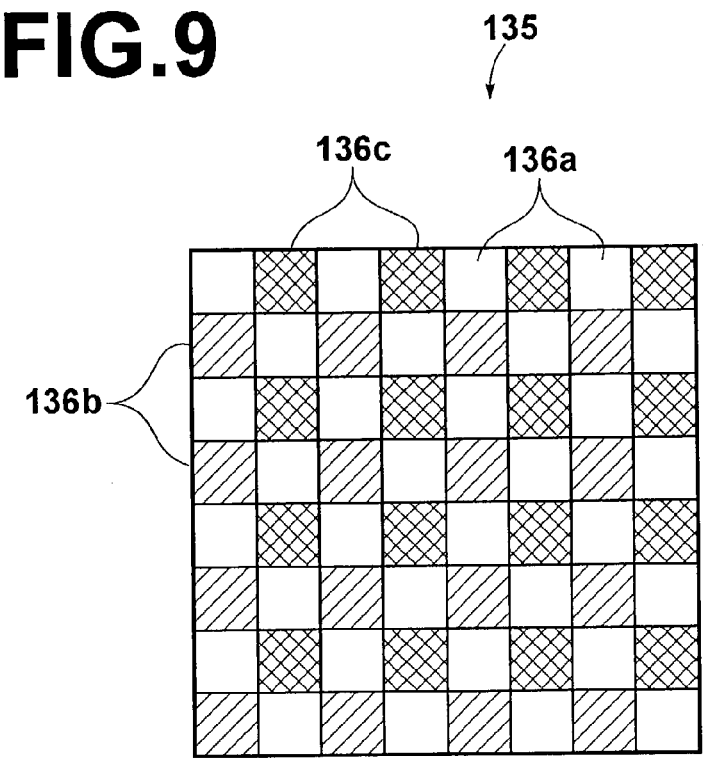
FIG. 9 is a view showing the mosaic filter employed in the fluorescence endoscope of the fourth embodiment.

As shown in FIG. 9, the mosaic filter 135 comprises a plurality of fine optical filters 136a each being a band-pass filter transmitting light in a wavelength band of 430 nm to 530 nm, a plurality of fine optical filters 136b each being a band-pass filter transmitting light in a wavelength band of 430 nm to 700 nm, a plurality of fine optical filters 136c each being a band-pass filter transmitting light in the entire wavelength band, which are arranged in a mosaic pattern. Each optical filter is in one-to-one correspondence with a pixel of the CCD image taking device 117. The optical filter 136a is for obtaining narrow-band fluorescence image data with the stimulating light Le1 projected onto the object part 1, the optical filter 136b is for obtaining broad-band fluorescence image data with the stimulating light Le1 projected onto the object part 1 and the optical filter 136c is for obtaining the IR reflection image data and ordinary image data.

The illumination unit 23 comprises a stimulating light source unit comprising a Ga—N semiconductor laser 201 which emits the stimulating light Le1 of a wavelength of 410 nm and a power source 202 for the semiconductor laser 201, a stimulating light source unit comprising a Ga—N semiconductor laser 211 which emits the stimulating light Le3 of a wavelength of 360 nm and a power source 212 for the semiconductor laser 204, a reference light source unit comprising a reference light source 207 which emits the reference light Ls and a power source 208 for the reference light source 207, and a sequential light source unit comprising a white light source 231, a power source 232 for the white light source 231, a color switching filter 234 for separating red light Lr, green light Lg and blue light Lb from white light in sequence, and a filter drive system 236 which rotates the color switching filter 234.

Figure 10:
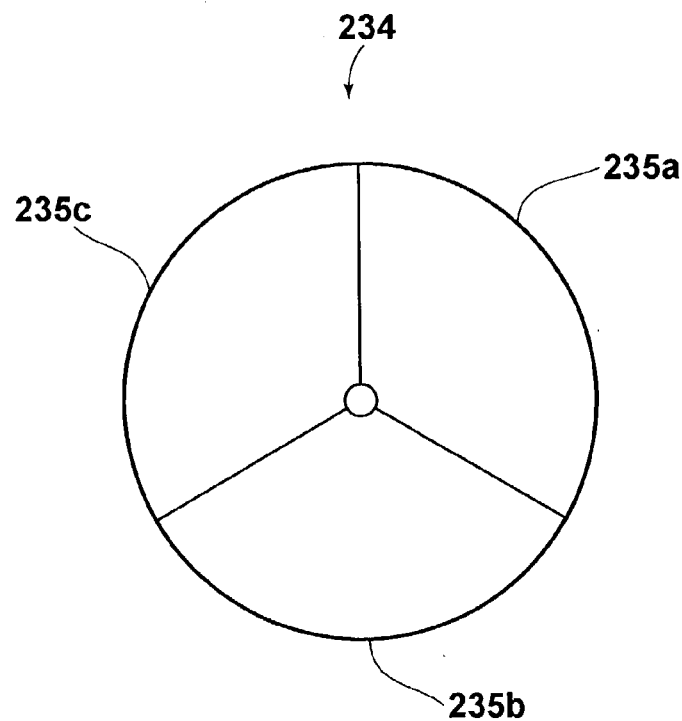
FIG. 10 is a view showing the color switching filter employed in the fluorescence endoscope of the fourth embodiment.

As shown in FIG. 10, the color switching filter 234 comprises a red filter 235a transmitting red light Lr, a green filter 235b transmitting green light Lg and a blue filter 235c transmitting blue light Lb.

The ordinary image processing unit 33 comprises a signal processing circuit 331 which processes image data obtained by pixels of the CCD image taking device 117 corresponding to the optical filters 136c when red light Lr, green light Lg and blue light Lb are projected onto the object part 1, an A/D convertor 332 which digitizes the image data output from the signal processing circuit 331, an image memory 333 which stores digitized red image data, digitized green image data and digitized blue image data, an ordinary image generating section 334 which generates ordinary image data on the basis of the three pieces of digitized color image data stored in the image memory 333, and a video signal processing circuit 335 which converts the ordinary image data output from the ordinary image generating section 334 to a video signal and outputs the video signal.

The fluorescence image processing unit 43 comprises a signal processing circuit 401 which processes the signal obtained by the CCD image taking device 117 when the stimulating light Le1 or the reference light Ls is projected onto the object part 1, thereby obtaining image data; an A/D convertor 402 which digitizes the image data output from the signal processing circuit 401; an image memory 431 which stores in different storage areas narrow-band fluorescence image data (Le1) obtained by taking the fluorescence image Zj1, broad-band fluorescence image data (Le1) fluorescence image Zj1, and the IR reflection image data obtained by taking the IR reflection image; a fluorescence intensity calculating section 432 which calculates the normalized intensity of fluorescence (Le1) as the first characteristic value by dividing the value of each pixel of the narrow-band fluorescence image data (Le1) by the value of the corresponding pixel of the broad-band fluorescence image data (Le1); a fluorescence diagnostic image generating section 433 which allocates to the pixels color information on the basis of the normalized intensity of fluorescence (Le1) and brightness information on the basis of the value of the corresponding pixel of the IR reflection image data, and generates fluorescence diagnostic image data on the basis of combination of the color information and the brightness information; and a video signal processing circuit 434 which converts the fluorescence diagnostic image data to a video signal and outputs the video signal to the monitor 70.

The optical path separating unit 50 comprises a dichroic mirror 501 which causes the stimulating light Le3 radiated from the Ga—N semiconductor laser 213 to enter the quartz fiber 53 and causes fluorescence propagated through the quartz fiber 53 to enter the disturbance calculation unit 51.

The disturbance calculation unit 51 comprises a stimulating light cut filter 511 which cuts wavelengths near the stimulating light Le3 from fluorescence propagated through the quartz fiber 53, a variable filter means 513 which selectively transmits fluorescence in a wavelength band of 430 nm to 490 nm or in a wavelength band of 430 nm to 700 nm out of fluorescence passing through the stimulating light cut filter 511, a filter drive system 515 which rotates the variable filter means 513, a photodetector 516 which measures the intensity F1 of fluorescence in the wavelength band of 430 nm to 490 nm passing through the variable filter means 513 and the intensity F2 of fluorescence in the wavelength band of 430 nm to 700 nm passing through the variable filter means 513, a data memory 517 which stores the intensity F1 of fluorescence and the intensity F2 of fluorescence measured by the photodetector 516, a fluorescence intensity calculating section 518 which calculates the normalized intensity F1/F2 of fluorescence as the second characteristic value by dividing the intensity F1 of fluorescence by the intensity F2 of fluorescence, a storage section 519 which stores as the reference values an average Av3 and a standard deviation St3 of the normalized intensities F1/F2 of fluorescences (Le2) obtained in advance from a plurality of clean organic tissues, a fluorescence diagnostic information generating section 520 which calculates the degree of influence B3 of the disturbance factor on the basis of the normalized intensity of fluorescence (F1/F2) calculated by the fluorescence intensity calculating section 518 and the reference values.

Figure 11:
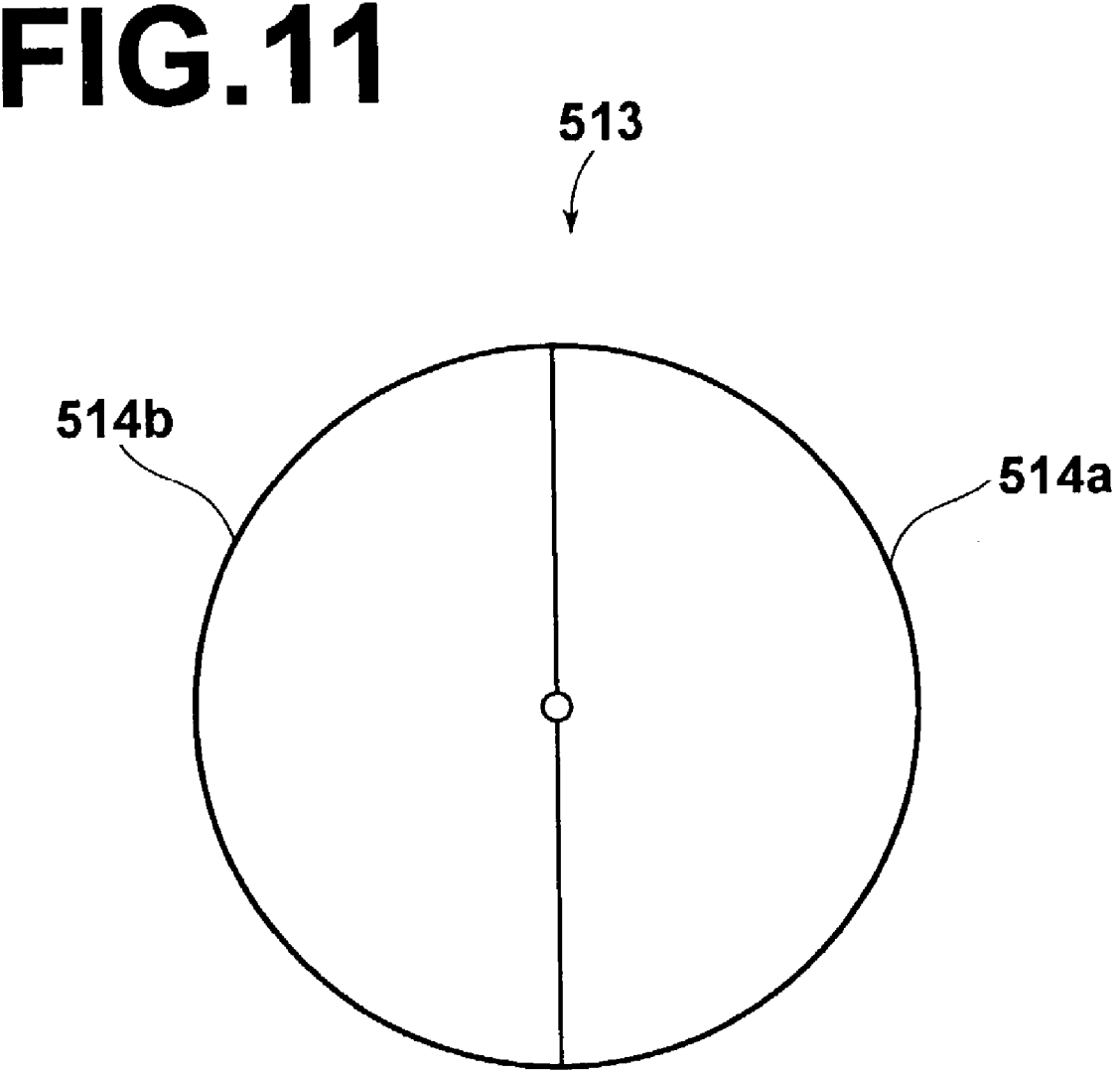
FIG. 11 is a view showing the variable filter means employed in the fluorescence endoscope of the fourth embodiment.

As shown in FIG. 11, the variable filter means 513 comprises a narrow-band optical filter 514*a* which transmits light in a wavelength band from 430 nm to 490 nm and a broad-band optical filter 514*b* which transmits light in a wavelength band from 430 nm to 700 nm.

The controller 63 is connected to each part and controls the timing of operation of the parts.

Operation of this endoscope will be described, hereinbelow. The viewer inserts the scope section 13 into the body cavity of the patient and leads the front end of the scope section 13 near to the object part 1. Operation in the ordinary image mode will be described first. The viewer selects the ordinary image mode by the use of the input system 631. In the ordinary image mode, the sequential light is projected onto the object part 1 and an ordinary image is taken. Ordinary image data is generated and an ordinary color image of the object part 1 is displayed on the monitor 70.

Obtaining a red image will be described first. The power source 232 for the white light source 231 is driven under the control of a signal from the controller 63, and white light is radiated from the white light source 231. The white light is condensed by a condenser lens 237 and impinges upon the color switching filter 234. When a red image is to be taken, the color switching filter 234 is rotated under the control of a signal from the controller 63 so that the red filter 235*a* is on the optical path of the white light. After passing through the red filter 235*a*, the white light is turned to red light Lr, and the red light Lr is projected onto the object part 1 through the illumination lens 104 by way of the light guide 132*c*.

The part of the red light Lr reflected at the object part 1 is condensed by the condenser lens 114 and imaged on the CCD image taking device 117 as a red reflection image Zr by way of the prism 118. Signal components obtained through pixels corresponding to the optical filters of the mosaic filter 135 out of the image data output from the CCD image taking device 117 are processed by the signal processing circuit 331 of the ordinary image processing unit 33 and are output as the red image data. The other signal components of the image data output from the CCD image taking device 117 are discarded. The red image data is digitized by the A/D convertor 332 and stored in the memory area for the red image in the image memory 333. In a similar manner, a green image data and a blue image data are obtained and stored in the memory areas for the respective images in the image memory 333.

After the red image data, the green image data and the blue image data are stored in the image memory 333, the ordinary image generating section 334 generates ordinary image data on the basis of the three pieces of color image data stored in the image memory 333, and the video signal processing circuit 335 converts the ordinary image data to a video signal and outputs the video signal to the monitor 70. The monitor 70 displays an ordinary color image.

When the fluorescence diagnosis mode is selected, the power source 202 is operated under the control of a signal from the controller 63 and the Ga—N semiconductor laser 201 radiates a stimulating light Le1 of a wavelength of 410 nm. The stimulating light Le1 enters the light guide 132*a* through a lens 203, propagates to the front end of the scope section 10, and then is projected onto the object part 1 by the illumination lens 104.

Fluorescence emitted from the object part 1 upon exposure to the stimulating light Le1 is condensed by the condenser lens 114 to enter the image fiber 103 and imaged on the CCD image taking device 117 as the fluorescence image Zj1 by way of the stimulating light cut filter 119, the prism 118 and the mosaic filter 135. The stimulating light cut filter 119 cuts wavelengths not longer than 420 nm and accordingly the reflected stimulating light Le1 is prevented from impinging upon the CCD image taking device 117. The CCD image taking device 117 photoelectrically converts the fluorescence image Zj1 into an image signal.

The image signal output from the CCD image taking device 117 is processed by the signal processing circuit 401, is digitized by the A/D convertor 402 and is stored in the image memory 431 divided into the narrow-band fluorescence image data (Le1) obtained through the optical filters 136*a* and the broad-band fluorescence image data (Le1) obtained through the optical filters 136*b*.

Taking the IR reflection image Zs will be described, hereinbelow. The power source 208 is operated under the control of a signal from the controller 63 and the reference light source 207 radiates near-infrared light as the reference light Ls. The reference light Ls enters the light guide 132b through a lens 209, propagates to the front end of the scope section 13, and then is projected onto the object part 1 by the illumination lens 104.

The reflected reference light Ls reflected by the object part 1 is condensed by the condenser lens 114 and focused on the CCD image taking device 117 as the IR reflection image Zs by way of the prism 118 and the mosaic filter 135. The CCD image taking device 117 photoelectrically converts the IR reflection image Zs into an image signal. The image signal output from the CCD image taking device 117 is processed by the signal processing circuit 401 and is digitized by the A/D convertor 402. Image data representing the light passing through the optical filters 136c is stored in the image memory 431 as the IR reflection image data.

When the narrow-band fluorescence image data (Le1), the broad-band fluorescence image data (Le1), and the IR reflection image data are stored in the image memory 431, the fluorescence intensity calculating section 432 calculates the normalized intensity of fluorescence (Le1) by dividing the value of each pixel of the narrow-band fluorescence image data (Le1) stored in the image memory 431 by the value of the adjacent pixel of the broad-band fluorescence image data (Le1) stored in the image memory 431.

The fluorescence diagnostic image generating section 433 allocates color information to the pixels on the basis of the normalized intensities of fluorescence (Le1). Generally, the normalized intensity of fluorescence emitted from a normal tissue is large and the normalized intensity of fluorescence emitted from a diseased tissue is small. Accordingly, by setting the pseudo-color to represent the normalized intensity of fluorescence, for instance, by allocating pseudo-color to the pixels so that the color of the pixels varies from green to red as the normalized intensity of fluorescence decreases, whether the object part 1 is a normal tissue or a diseased tissue can be easily seen from the fluorescence diagnostic image.

When the pixel 2 displayed in red cannot be determined whether it is a clean diseased tissue or an unclean tissue on the fluorescence diagnostic image, the viewer leads the front end of the quartz fiber 53 near to the object part 1 and switches the endoscope to the disturbance measurement mode by the input system 631. When the disturbance measurement mode is selected, the power source 212 is operated under the control of a signal from the controller 63 and the Ga—N semiconductor laser 211 radiates a stimulating light Le3 of a wavelength of 360 nm. The stimulating light Le3 passes through a lens 213 and impinges upon the dichroic mirror 501. The stimulating light Le3 is reflected by the dichroic mirror 501 and enters the quartz fiber 53 through a lens 502. Then the stimulating light Le3 is projected onto the object part 1 from the front end of the quartz fiber 53.

Fluorescence L3 emitted from the object part 1 upon exposure to the stimulating light Le3 impinges upon the dichroic mirror 501 by way of the quartz fiber 53 and the lens 502 and passes through the dichroic mirror 501. After passing through the dichroic mirror 501, the fluorescence L3 impinges upon the variable filter means 513 by way of stimulating light cut filter 511 and a lens 512. The stimulating light cut filter 511 cuts wavelengths not longer than 420 nm and accordingly the stimulating light Le3 reflected at the object part 1 is prevented from impinging upon the variable filter means 513.

The fluorescence L3 impinges upon the photodetector 516 after passing through the optical filter 514a or 514b, which is selectively inserted into the optical path of the fluorescence L3 under the control of the controller 63. The photodetector 516 measures the narrow-band intensity F1, that is, the intensity of the fluorescence L3 passing through the optical filter 514a, and the broad-band intensity F2, that is, the intensity of the fluorescence L3 passing through the optical filter 514b, and outputs the measured intensities F1 and F2 to the data memory 517. The data memory 517 stores the measured intensities F1 and F2 in the respective memory areas.

The fluorescence intensity calculating section 518 calculates the normalized intensity F1/F2 of fluorescence by dividing the narrow-band intensity F1 of fluorescence by the broad-band intensity F2 of fluorescence.

The fluorescence diagnostic information generating section 520 calculates the degree of influence B3 of the disturbance factor according to the following formula on the basis of the normalized intensity of fluorescence (F1/F2) and the average Av3 and the standard deviation St3 of the normalized intensities of fluorescences which have been obtained from a plurality of clean tissues.

$$B3=\{(NF3-Av3)/St3\}^2$$

Further, the fluorescence diagnostic information generating section 520 outputs the calculated degree of influence B3 of the disturbance factor to the monitor 70 and the monitor 70 displays the calculated degree of influence B3 of the disturbance factor in numeric representation. That is, when the value of the degree of influence B3 of the disturbance factor is small, the pixel 2 may be considered to be clean and when the value of the degree of influence B3 of the disturbance factor is large, the pixel 2 may be considered to be unclean.

As can be understood from the description above, by viewing the fluorescence diagnostic image and the value of the degree of influence B3 of the disturbance factor, it is possible to determine whether the object part is a clean diseased tissue or an unclean tissue stained with a disturbance factor which emits, upon exposure to the stimulating light Le1, fluorescence which resembles in shape of spectrum fluorescence emitted from a clean diseased tissue. Accordingly, mistaking an unclean tissue for a clean diseased tissue is suppressed and the tissue-property distinguishing accuracy can be improved.

Figure 12:
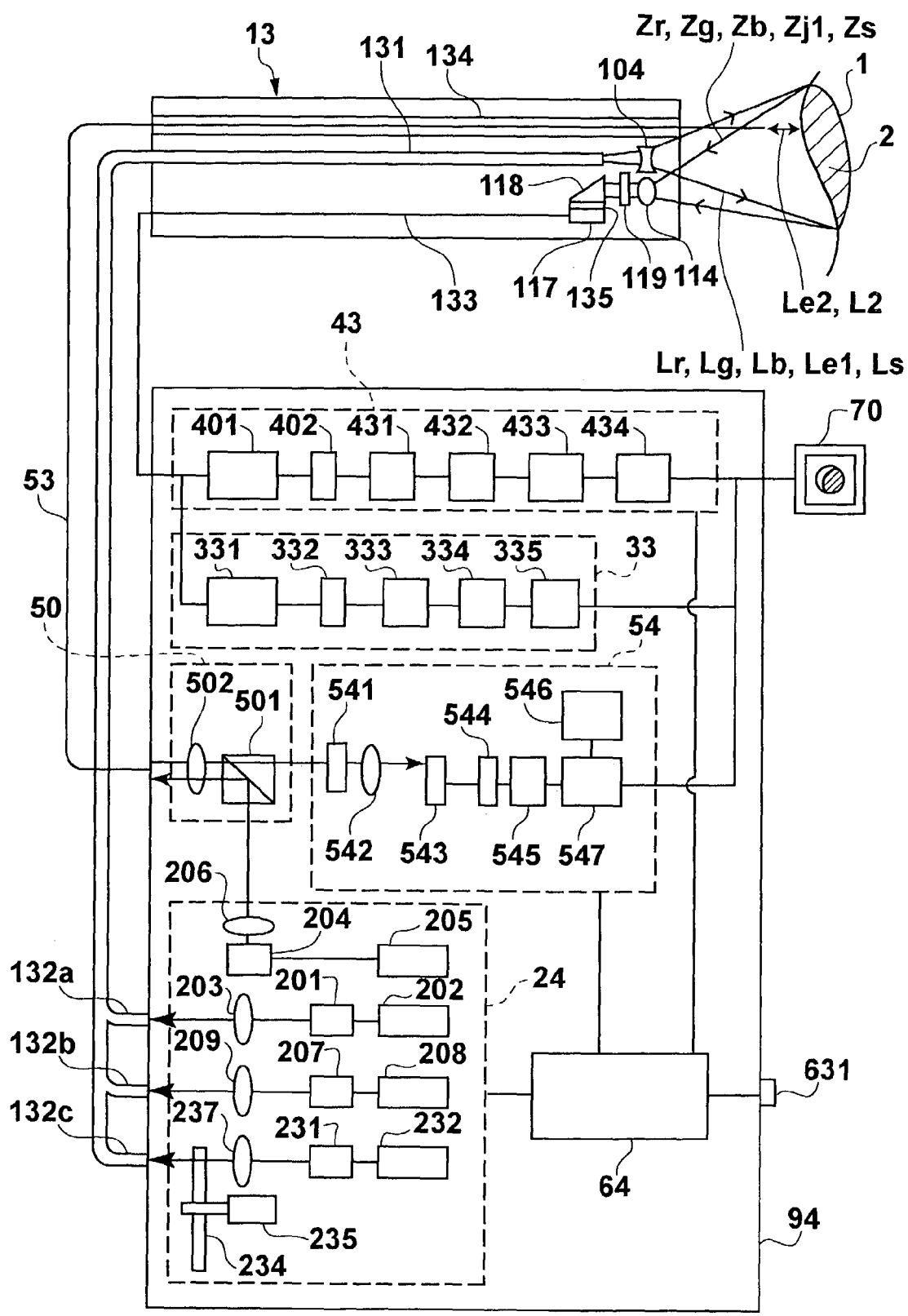
FIG. 12 is a view showing in brief a fluorescence endoscope in accordance with a fifth embodiment of the present invention.

An endoscope in accordance with a fifth embodiment of the present invention will be described with reference to FIG. 12, hereinbelow. In FIG. 12, the elements analogous to those shown in FIG. 8 are given the same reference numerals and will not be described unless necessary.

The fluorescence endoscope works in one of an ordinary image mode, a fluorescence diagnosis mode and a disturbance measurement mode which are switched by operation of an input system 631. In the ordinary image mode, an ordinary color image is displayed on the monitor 70. In the fluorescence diagnosis mode, stimulating light Le1 of a wavelength of 410 nm is projected onto an object part 1, and a fluorescence diagnostic image is displayed on a monitor 70, the fluorescence diagnostic image being a pseudo-color image obtained by allocating pseudo-colors on the basis of a normalized intensity of fluorescence (Le1) emitted from the object part 1, and in the disturbance measurement mode, stimulating light Le2 of a wavelength of 500 nm is projected onto the object part 1 through a quartz fiber 53, fluorescence emitted from the object part 1 upon exposure to the stimulating light Le2 is detected through a quartz fiber, the degree of influence B4 of the disturbance factor is calculated on the basis of the normalized intensity of fluorescence (Le2)

emitted from the object part 1 and the degree of influence B4 of the disturbance factor is displayed on the monitor 70.

In the disturbance measurement mode, an intensity F3 of fluorescence of a wavelength of 550 nm is obtained on the basis of fluorescence emitted from each pixel 2 of the object part 1 upon exposure to the stimulating light Le2 of a wavelength of 500 nm, an intensity F4 of fluorescence of a wavelength of 570 nm is obtained on the basis of fluorescence emitted from each pixel 2 of the object part 1 upon exposure to the stimulating light Le2 of a wavelength of 500 nm, the ratio of intensity of fluorescence F3/F4 is obtained by dividing the intensity F3 by the intensity F4, and the degree of influence B4 of the disturbance factor is calculated on the basis of the ratio of intensity of fluorescence F3/F4 and reference values which have been stored in a storage section 546.

The fluorescence endoscope of the fifth embodiment comprises, as shown in FIG. 12, a scope section 13 which is inserted into a suspected diseased part of a patient, an illumination unit 24 provided with sources of the stimulating light Le1 of a wavelength of 410 nm, the stimulating light Le2 of a wavelength of 500 nm, the reference light Ls, and the sequential light (the red light Lr, green light Lg, and blue light Lb projected onto the object part 1 in sequence in order to take an ordinary color image), an ordinary image processing unit 33 which outputs ordinary image data, a fluorescence image processing unit 43 which outputs fluorescence diagnostic image data, an optical path separating unit 50 which separates the optical path of the stimulating light Le2 and the optical path of the detected fluorescence, a disturbance calculation unit 54 which calculates the degree of influence B4 of the disturbance factor on the basis of the ratio of intensity of fluorescence F3/F4 and reference values which have been stored, a controller 64 which is connected to the units and controls the timing of operation of the units, the input system 631 connected to the controller 63, the monitor 70 and the quartz fiber 53 which propagates fluorescence emitted from the pixels 2 of the object part 1.

The illumination unit 24, the ordinary image processing unit 33, the fluorescence image processing unit 43, the optical path separating unit 50, the disturbance calculation unit 54 and the controller 64 form a processor section 94. The scope section 13 and the processor section 94 are connected by way of a connector (not shown), the quartz fiber 53 and the processor section 94 are connected by way of a connector (not shown) and the processor section 94 and the monitor 70 are connected by way of a connector (not shown).

The illumination unit 24 comprises a stimulating light source unit comprising a Ga—N semiconductor laser 201 which emits the stimulating light Le1 of a wavelength of 410 nm and a power source 202 for the semiconductor laser 201, a stimulating light source unit comprising a Ga—N semiconductor laser 204 which emits the stimulating light Le2 of a wavelength of 500 nm and a power source 205 for the semiconductor laser 204, a reference light source unit comprising a reference light source 207 which emits the reference light Ls and a power source 208 for the reference light source 207, and a sequential light source unit comprising a white light source 231, a power source 232 for the white light source 231, a color switching filter 234 for separating red light Lr, green light Lg and blue light Lb from white light in sequence, and a filter drive system 236 which rotates the color switching filter 234.

The disturbance calculation unit 54 comprises a stimulating light cut filter 541 which cuts wavelengths shorter than 510 nm (including the wavelength of the stimulating light Le2) from fluorescence propagated through the quartz fiber 53, a spectrum detector 543 which measures the spectral intensity of fluorescence passing through the stimulating light cut filter 541, a data memory 544 which stores the intensity of fluorescence measured by the spectrum detector 543, a fluorescence intensity ratio calculating section 545 which calculates the ratio F3/F4 of fluorescence intensity as the second characteristic value by dividing the intensity F3 of fluorescence of a wavelength of 550 nm by the intensity F4 of fluorescence of a wavelength of 570 nm, a storage section 546 which stores as the reference values an average Av3 and a standard deviation St3 of the ratio F3/F4 of intensity of fluorescences (Le2) obtained in advance from a plurality of clean organic tissues, a fluorescence diagnostic information generating section 547 which calculates the degree of influence B4 of the disturbance factor on the basis of the ratio F3/F4 of fluorescence intensity calculated by the fluorescence intensity ratio calculating section 545 and the reference values.

Operation of this endoscope will be described, herein below. When it is impossible to determine whether a part displayed in red is a clean diseased tissue or a false diseased tissue, the viewer leads the front end of the quartz fiber 53 to the part and manually switches the endoscope to the disturbance measurement mode by the input system 631.

When the disturbance measurement mode is selected, the power source 205 is operated under the control of a signal from the controller 64 and the Ga—N semiconductor laser 204 radiates a stimulating light Le2 of a wavelength of 500 nm. The stimulating light Le2 passes through a lens 203 and impinges upon the dichroic mirror 501. The stimulating light Le2 is reflected by the dichroic mirror 501 and enters the quartz fiber 53 through a lens 502. Then the stimulating light Le2 is projected onto the object part 1 from the front end of the quartz fiber 53.

Fluorescence L2 emitted from the object part 1 upon exposure to the stimulating light Le2 impinges upon the dichroic mirror 501 by way of the quartz fiber 53 and the lens 502 and passes through the dichroic mirror 501. After passing through the dichroic mirror 501, the fluorescence L2 impinges upon the spectrum detector 543 by way of stimulating light cut filter 511 and a lens 512. The spectrum detector 543 measures the spectrum of the detected fluorescence L2, and outputs the measured spectrum to the data memory 544. The fluorescence intensity ratio calculating section 545 calculates the ratio F3/F4 of fluorescence intensity by dividing the intensity F3 of fluorescence of a wavelength of 550 nm by the intensity F4 of fluorescence of a wavelength of 570 nm.

The fluorescence diagnostic information generating section 547 calculates the degree of influence B4 of the disturbance factor according to the following formula on the basis of the ratio F3/F4 of fluorescence intensity and the average Av4 and the standard deviation St4 of the ratio F3/F4 of fluorescences which have been obtained from a plurality of clean tissues.

$$B4=\{(F3/F4-Av4)/St4\}^2$$

Further, the fluorescence diagnostic information generating section 547 outputs the calculated degree of influence B4 of the disturbance factor to the monitor 70 and the monitor 70 displays the calculated degree of influence B4 of the disturbance factor in numeric representation. That is, when the value of the degree of influence B4 of the disturbance factor is small, the pixel 2 may be considered to be clean and when the value of the degree of influence B4 of the disturbance factor is large, the pixel 2 may be considered to be unclean.

As can be understood from the description above, by viewing the fluorescence diagnostic image and the value of the degree of influence B4 of the disturbance factor, it is possible to determine whether the object part is a clean diseased tissue or an unclean tissue. Accordingly, mistaking an unclean tissue for a clean diseased tissue is suppressed and the tissue-property distinguishing accuracy can be improved.

Figure 2:
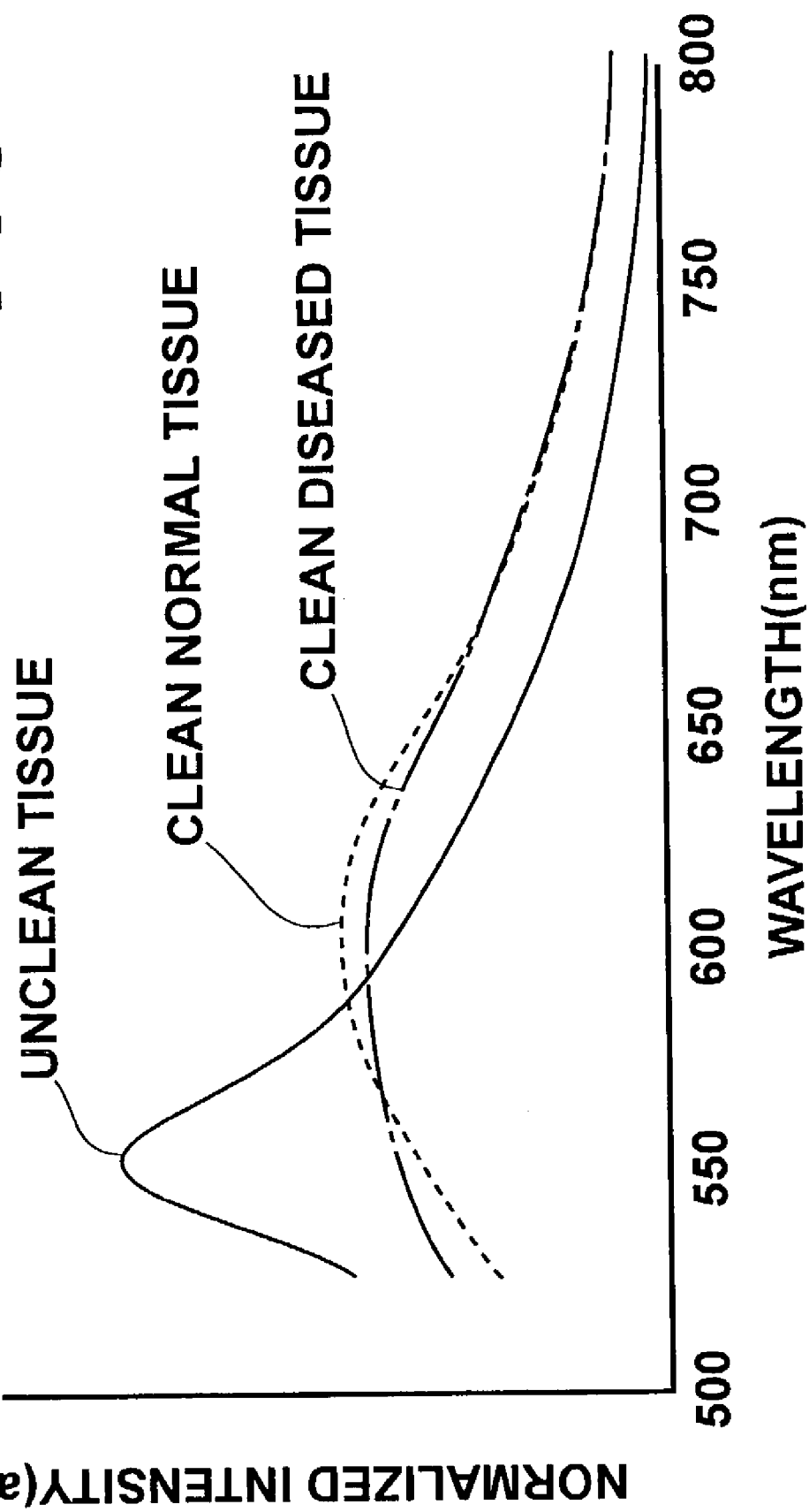
FIG. 2 is a view showing the shapes of spectra of fluorescences emitted from a clean normal tissue, a clean diseased tissue and an unclean tissue upon exposure to a stimulating light of 500 nm.

As can be understood from FIG. 2, the spectrum of fluorescence emitted from an unclean tissue (solid line) upon exposure to the stimulating light of 500 nm has a peak of intensity near to 550 nm, whereas the spectrum of fluorescence emitted from a clean normal or diseased tissue (dotted line or chained line) has a peak of intensity near to 610 nm. Accordingly, there generally exists a great difference between the ratio F3/F4 of fluorescence intensity obtained from fluorescence emitted from an unclean tissue upon exposure to the stimulating light of 500 nm and that obtained from fluorescence emitted from a clean tissue, whereby the tissue-property distinguishing accuracy can be further improved.

Figure 1:
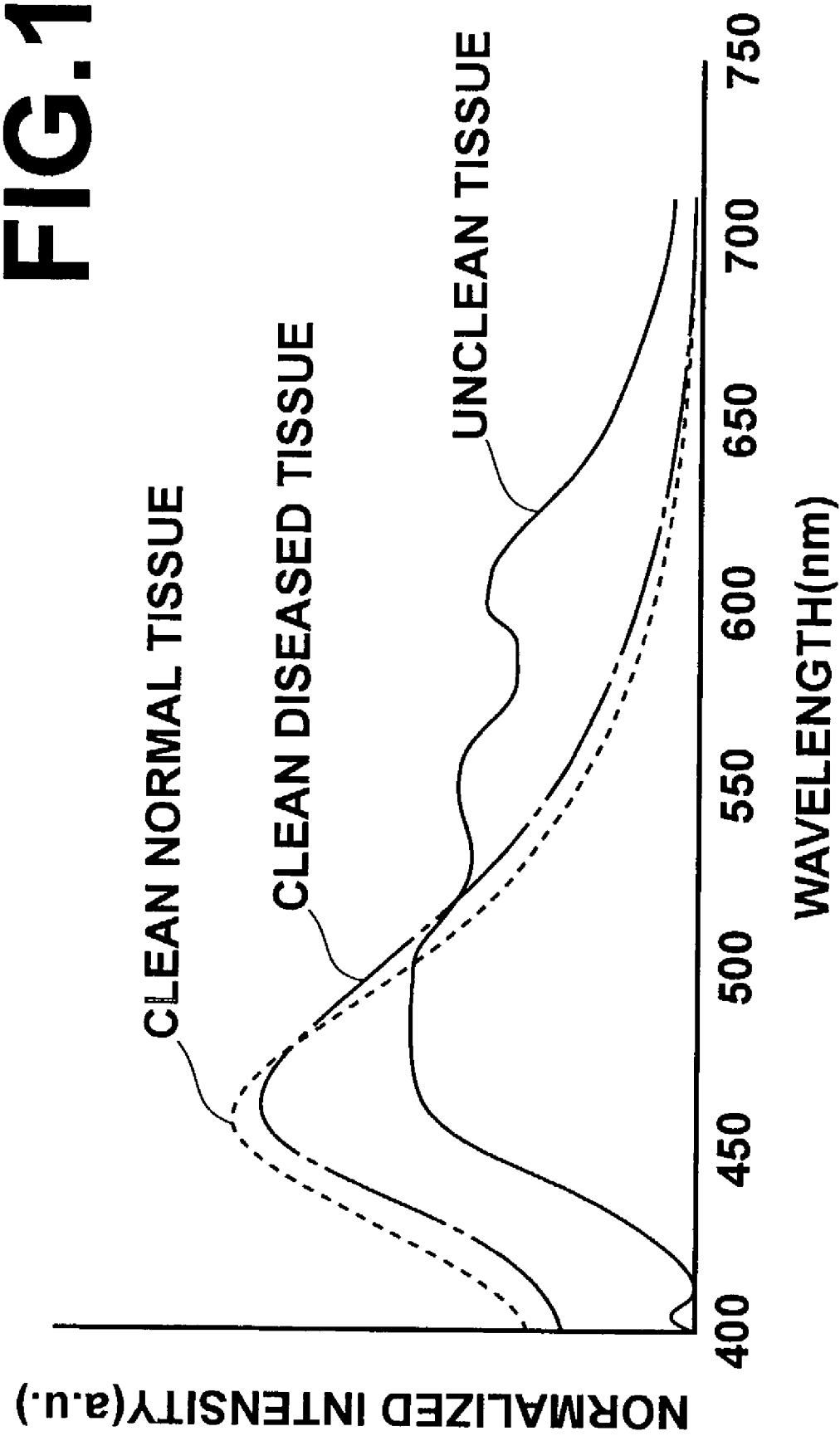
FIG. 1 is a view showing the shapes of spectra of fluorescences emitted from a clean normal tissue, a clean diseased tissue and an unclean tissue upon exposure to a stimulating light of 360 nm.

In place of a stimulating light of 500 nm, a stimulating light of 360 nm may be employed as the stimulating light Le2 while the ratio F3'/F4' of fluorescence intensity obtained by dividing the intensity F3' of fluorescence of a wavelength of 460 nm by the intensity F4' of fluorescence of a wavelength of 490 nm is used to calculate the degree of influence B4 of the disturbance factor. As shown in FIG. 1, the intensity of fluorescence near 460 nm is close to that near 490 nm in the spectrum of fluorescence emitted from an unclean tissue (solid line) upon exposure to the stimulating light of 360 nm, whereas the spectrum of fluorescence emitted from a clean normal or diseased tissue (dotted line or chained line) upon exposure to the stimulating light of 360 nm has a peak of intensity near to 460 nm and accordingly, the intensity of fluorescence near 490 nm is lower than that near 460 nm. Accordingly, there generally exists a great difference between the ratio F3'/F4' of fluorescence intensity obtained from fluorescence emitted from an unclean tissue upon exposure to the stimulating light of 360 nm and that obtained from fluorescence emitted from a clean tissue, whereby the tissue-property can be distinguished at a high accuracy.

Though, in the endoscopes of the fourth and fifth embodiments, a fluorescence diagnostic image or an ordinary image is displayed, the endoscopes may be arranged to display only a fluorescence diagnostic image.

Though, in the endoscopes of the fourth and fifth embodiments, the degree of influence of the disturbance factor is displayed in numeric representation, the endoscopes may be arranged to judge whether each pixel 2 of the object part 1 is a clean tissue or an unclean tissue on the basis of the value NF of the normalized intensity of fluorescence and the average Av and the standard deviation St of the normalized intensities of fluorescences which have been obtained from a plurality of clean tissues and stored in the storage section and display the result of the judgment. That is, when the value NF of the normalized intensity of fluorescence satisfies the following formula, it is judged that the pixel 2 is a clean tissue.

$$Av-St<NF<Av+St$$

Though, in the fourth and fifth embodiments, the mosaic filter 135 comprises optical filters 136a transmitting light in a wavelength band of 430 to 530 nm, optical filters 136b transmitting light in a wavelength band of 430 nm to 700 nm, and optical filters 136c transmitting light in the entire wavelength band, the optical filters transmitting light in the entire wavelength band may be caused to double as the optical filters transmitting light in a wavelength band of 430 nm to 700 nm. In this case, the mosaic filter may comprise only two kinds of optical filters, which results in improvement of resolution and increase in amount of detected fluorescence.

Though, in the endoscope of the fifth embodiment, whether the pixel 2 is an unclean tissue or a clean tissue is judged on the basis of the ratio of the intensity of fluorescence at 550 nm to the intensity of fluorescence at 570 nm, the judgment may be made in other ways. For example, whether the pixel 2 is an unclean tissue or a clean tissue may be judged by a spectral analysis in which a spectrum of fluorescence intensity emitted from a known clean tissue is stored in advance and is compared with a spectrum of fluorescence intensity emitted from the pixel 2.

What is claimed is:

1. A method of generating fluorescence diagnostic information comprising the steps of
    detecting first fluorescence information on fluorescence emitted from an object part exposed to first stimulating light, obtaining a first characteristic value on the basis of the first fluorescence information, and outputting a first fluorescence diagnostic information reflecting the first characteristic value, and
    detecting second fluorescence information on fluorescence emitted from the object part exposed to second stimulating light, obtaining a second characteristic value on the basis of the second fluorescence information, and outputting a second fluorescence diagnostic information reflecting the second characteristic value,
    wherein the wavelength of the first stimulating light is such that when the first stimulating light is projected onto clean object parts different in properties, different first characteristic values are obtained on the basis of the respective pieces of fluorescence information on fluorescences emitted from the object parts, and
    the wavelength of the second stimulating light is such that when the second stimulating light is projected onto a clean object part and an unclean object part, different second characteristic values are obtained on the basis of the respective pieces of fluorescence information on fluorescences emitted from the clean object part and the unclean object part.

2. The method of generating fluorescence diagnostic information according to claim 1, wherein the second characteristic is a normalized intensity of fluorescence reflecting shape of spectrum of fluorescence, and wherein the shape of spectrum of fluorescence of the clean object part has a peak with a higher intensity than intensity of fluorescence of the unclean object part and the shape of spectrum of fluorescence of the unclean object part has a relatively flat curve at a lower intensity than intensity of fluorescence of the clean object part.

3. The method of generating fluorescence diagnostic information according to claim 1, wherein the second characteristic is a normalized intensity of fluorescence reflecting shape of spectrum of fluorescence, and wherein the shape of spectrum of fluorescence of the unclean object part has a peak with a higher intensity than intensity of fluorescence of the clean object part and the shape of spectrum of fluorescence of the clean object part has a round curve at a lower intensity than intensity of fluorescence of the unclean object part.

4. The method of generating fluorescence diagnostic information according to claim 1, wherein the first characteristic indicates whether the object part is a diseased tissue or normal tissue and wherein the second characteristic indicates whether the object part is unclean, where the object part is unclean when the object part has been stained with a disturbance factor comprising at least one of blood, mucus, digestive fluid, saliva, foam, and residue.

5. The method of generating fluorescence diagnostic information according to claim 1, wherein fluorescence emitted from an unclean object part upon exposure to 360 nm is different in shape of spectrum from fluorescence emitted from a clean object part upon exposure to 360 nm.

6. The method of generating fluorescence diagnostic information according to claim 1, wherein fluorescence emitted from an unclean object part upon exposure to 500 nm is different in shape of spectrum from fluorescence emitted from a clean object part upon exposure to 500 nm.

7. The method of generating fluorescence diagnostic information according to claim 6, wherein fluorescence emitted from a diseases object part upon exposure to 410 nm is different from fluorescence emitted from a normal object part upon exposure to 410 nm.

8. An apparatus for generating fluorescence diagnostic information comprising
a first stimulating light projecting means which projects first stimulating light onto an object part,
a first detecting means which detects first fluorescence information on fluorescence emitted from the object part exposed to the first stimulating light,
a first characteristic value obtaining means which obtains a first characteristic value on the basis of the first fluorescence information,
a second stimulating light projecting means which projects second stimulating light onto the object part,
a second detecting means which detects second fluorescence information on fluorescence emitted from the object part exposed to the second stimulating light,
a second characteristic value obtaining means which obtains a second characteristic value on the basis of the second fluorescence information, and
a fluorescence diagnostic information generating means which outputs a fluorescence diagnostic information reflecting the first and second characteristic values,
wherein the wavelength of the first stimulating light is such that when the first stimulating light is projected onto clean object parts different in properties, different first characteristic values are obtained on the basis of the respective pieces of fluorescence information on fluorescences emitted from the object parts, and
the wavelength of the second stimulating light is such that when the second stimulating light is projected onto a clean object part and an unclean object part, different second characteristic values are obtained on the basis of the respective pieces of fluorescence information on fluorescences emitted from the clean object part and the unclean object part.

9. The apparatus for generating fluorescence diagnostic information according to claim 8, wherein the first characteristic indicates whether the object part is a diseased tissue or normal tissue and wherein the second characteristic indicates whether the object part is unclean, where the object part is unclean when the object part has been stained with a disturbance factor comprising at least one of blood, mucus, digestive fluid, saliva, foam, and residue.

10. An apparatus as defined claim 8 in which the wavelength of the first stimulating light is near 410 nm and the wavelength of the second stimulating light is in the range of 350 nm to 390 nm or in the range of 470 nm to 520 nm.

11. An apparatus as defined claim 8 in which the first characteristic value is a normalized intensity of fluorescence reflecting the shape of spectrum of fluorescence or the yield of fluorescence and the second characteristic value is a normalized intensity of fluorescence reflecting the shape of spectrum of fluorescence or the yield of fluorescence.

12. An apparatus as defined in claim 8 in which the fluorescence diagnostic information generating means comprises a storage means which stores a first reference value created in advance on the basis of a first characteristic value obtained from at least one of a known clean normal tissue and a known clean diseased tissue, and a second reference value created in advance on the basis of a second characteristic value obtained from at least one of a known clean tissue and a known unclean tissue, and
a judgment means which judges whether the object part is on the side of the known clean diseased part on the basis of a first characteristic value obtained from the object part and the first reference value, and judges whether the object part is on the side of the known unclean part on the basis of a second characteristic value obtained from the object part and the second reference value,
and outputs as the fluorescence diagnostic information the result of judgment of the judgment means.

13. An apparatus as defined claim 12 in which the first characteristic value is a normalized intensity of fluorescence reflecting the shape of spectrum of fluorescence or the yield of fluorescence and the second characteristic value is a normalized intensity of fluorescence reflecting the shape of spectrum of fluorescence or the yield of fluorescence.

14. An apparatus as defined claim 12 in which the wavelength of the first stimulating light is near 410 nm and the wavelength of the second stimulating light is in the range of 350 nm to 390 nm or in the range of 470 nm to 520 nm.

15. A method of generating fluorescence diagnostic information comprising:
detecting first fluorescence information on fluorescence emitted from an object part exposed to a first stimulating light;
detecting a reflectance image information on an intensity of a reference light reflected from the object part exposed to a reference light;
obtaining a first characteristic value based on the first fluorescence information and the reflectance image information, said first characteristic value indicates a state of the object part;
outputting a first fluorescence diagnostic information reflecting the first characteristic value;
when a predetermined state of the object part is indicated by the first characteristic,
detecting second fluorescence information on fluorescence emitted from the object part exposed to a second stimulating light,
obtaining a second characteristic value on the basis of the second fluorescence information, the second characteristic value indicates whether the object part is a clean object part or an unclean object part, and
outputting a second fluorescence diagnostic information reflecting the second characteristic value, wherein the object part is unclean when the object part is stained with a disturbance factor.

16. The method according to claim 15, wherein said outputting the first fluorescence diagnostic information comprises determining a first or second color for each pixel based on the first characteristic value and determining a brightness of each pixel based on the reflectance image information, and wherein said outputting the second fluorescence diagnostic information comprises determining a third or fourth color for each pixel based on the second characteristic value, where the third or fourth color of each respective pixel is displayed on top of the first or second color of a corresponding pixel.

17. The method according to claim 15, wherein:
the predetermined state indicates that the object part is a diseased tissue,
when the first characteristic indicates that the object part is the diseased tissue, switching from a fluorescence detecting mode where the first characteristic is obtained to a disturbance judgment mode in which the second characteristic is determined, and
the second fluorescence information comprises two fluorescence image data, each formed of fluorescent light of a mutually different wavelength band.

18. The method according to claim 15, wherein the state of the object part is a diseased tissue or normal tissue and wherein the disturbance factor comprises a liquid or a substance.

19. The method according to claim 18, wherein the disturbance factor comprises one of blood, mucus, digestive fluid, saliva, foam, and residue.

20. An apparatus for generating fluorescence diagnostic information comprising
a first stimulating light projecting means which projects first stimulating light onto an object part,
a first detecting means which detects first fluorescence information on fluorescence emitted from the object part exposed to the first stimulating light,
a first characteristic value obtaining means which obtains a first characteristic value on the basis of the first fluorescence information,
a first fluorescence diagnostic information generating means which outputs a first fluorescence diagnostic information reflecting the first characteristic value,
a second stimulating light projecting means which projects second stimulating light onto the object part,
a second detecting means which detects second fluorescence information on fluorescence emitted from the object part exposed to the second stimulating light,
a second characteristic value obtaining means which obtains a second characteristic value on the basis of the second fluorescence information, and
a second fluorescence diagnostic information generating means which outputs a second fluorescence diagnostic information reflecting the second characteristic value,
wherein the wavelength of the first stimulating light is such that when the first stimulating light is projected onto clean object parts different in properties, different first characteristic values are obtained on the basis of the respective pieces of fluorescence information on fluorescences emitted from the object parts, and
the wavelength of the second stimulating light is such that when the second stimulating light is projected onto a clean object part and an unclean object part, different second characteristic values are obtained on the basis of the respective pieces of fluorescence information on fluorescences emitted from the clean object part and the unclean object part.

21. An apparatus as defined claim 20 in which the first characteristic value is a normalized intensity of fluorescence reflecting the shape of spectrum of fluorescence or the yield of fluorescence and the second characteristic value is a normalized intensity of fluorescence reflecting the shape of spectrum of fluorescence or the yield of fluorescence.

22. An apparatus as defined claim 20 in which the wavelength of the first stimulating light is near 410 nm and the wavelength of the second stimulating light is in the range of 350 nm to 390 nm or in the range of 470 nm to 520 nm.

23. A method of generating fluorescence diagnostic information comprising the steps of
detecting first fluorescence information on fluorescence emitted from an object part exposed to first stimulating light, and obtaining a first characteristic value on the basis of the first fluorescence information,
detecting second fluorescence information on fluorescence emitted from the object part exposed to second stimulating light, and obtaining a second characteristic value on the basis of the second fluorescence information, and
creating fluorescence diagnostic information reflecting the first and second characteristic values and outputting the fluorescence diagnostic information,
wherein the wavelength of the first stimulating light is such that when the first stimulating light is projected onto clean object parts different in properties, different first characteristic values are obtained on the basis of the respective pieces of fluorescence information on fluorescences emitted from the object parts, and
the wavelength of the second stimulating light is such that when the second stimulating light is projected onto a clean object part and an unclean object part, different second characteristic values are obtained on the basis of the respective pieces of fluorescence information on fluorescences emitted from the clean object part and the unclean object part.

* * * * *